US006267962B1

(12) United States Patent
Hart et al.

(10) Patent No.: US 6,267,962 B1
(45) Date of Patent: Jul. 31, 2001

(54) COMPOSITIONS AND METHODS OF TREATMENT USING PEAT DERIVATIVES

(75) Inventors: Ralph M. Hart, Lake Forest Park; Herman L. Jones; Veronica Lee Egelkrout Jones, both of Wenatchee; Sohail Malik, Redmond; Margaret A. Kenny, Edmonds, all of WA (US); Bernard Loev, Medford, NJ (US); James P. Harnisch, Mercer Island, WA (US)

(73) Assignee: C-P Technology Limited Partnership, Mill Creek, WA (US)

( * ) Notice: Subject to any disclaimer, the term of this patent is extended or adjusted under 35 U.S.C. 154(b) by 0 days.

(21) Appl. No.: 08/885,323

(22) Filed: Jun. 30, 1997

(Under 37 CFR 1.47)

Related U.S. Application Data

(63) Continuation of application No. 08/803,311, filed on Feb. 20, 1997, which is a continuation of application No. 08/531,099, filed on Sep. 20, 1995, now abandoned, which is a continuation of application No. 08/157,987, filed on Nov. 24, 1993, now abandoned, which is a continuation-in-part of application No. 07/969,793, filed on Oct. 29, 1992, now abandoned, which is a continuation-in-part of application No. 07/632,020, filed on Dec. 21, 1990, now abandoned.

(51) Int. Cl.$^7$ ................................................. A61K 35/78
(52) U.S. Cl. ..................... 424/195.1; 423/155; 423/158; 423/166; 423/179; 423/184; 423/193; 514/686; 514/825; 514/858; 514/861; 514/863; 514/886
(58) Field of Search .................................. 423/155, 158, 423/166, 179, 184, 193, 195.1; 514/686, 825, 858, 861, 863, 886

(56) References Cited

U.S. PATENT DOCUMENTS

| 3,864,475 | 2/1975 | Willard, Sr. ................................ 424/70 |
| 3,874,927 | 4/1975 | Willard, Sr. ........................... 134/25 A |
| 3,893,943 | 7/1975 | Willard, Sr. ............................. 252/428 |
| 3,915,738 | 10/1975 | Willard, Sr. ................................ 134/2 |
| 3,923,456 | 12/1975 | Willard, Sr. ............................. 8/137.5 |
| 3,925,053 | 12/1975 | Kealy ........................................... 71/29 |
| 3,931,031 | 1/1976 | Willard, Sr. .............................. 252/99 |
| 3,951,778 | 4/1976 | Willard, Sr. ......................... 208/11 LE |
| 3,984,540 | 10/1976 | Willard, Sr. ............................. 424/116 |
| 4,019,889 | 4/1977 | Kealy ........................................... 21/29 |
| 4,029,770 | 6/1977 | Willard, Sr. ............................. 424/127 |
| 4,059,691 | 11/1977 | Willard, Sr. ............................. 424/155 |
| 4,061,734 | 12/1977 | Willard, Sr. ............................. 424/155 |
| 4,067,712 | 1/1978 | Willard, Sr. ................................ 71/24 |
| 4,067,713 | 1/1978 | Willard, Sr. ................................ 71/24 |

(List continued on next page.)

FOREIGN PATENT DOCUMENTS

| 1043261 | 6/1990 | (CN) . |
| 2742030 | 9/1977 | (DE) . |
| 2846482 | 9/1979 | (DE) . |
| 3830333 | * 3/1990 | (DE) . |
| 0117223 | 11/1984 | (EP) ................................ C05F 11/02 |
| 0217975 | 4/1987 | (EP) ................................ A61K 7/48 |
| 0540945 | 5/1993 | (EP) ............................... A61K 35/10 |
| 4272030 | 7/1980 | (GB) ............................... A61K 35/10 |
| 2079599 | 1/1982 | (GB) . |
| 7896027 | 8/1978 | (JP) ................................ C04B 11/14 |

(List continued on next page.)

OTHER PUBLICATIONS

Bungariu et al., "Forme farmaceutice de uz extern cu un extract din turba de Stobor. Nota III Pudre," *Farmacia* XXII:5 (1974) (Entire Rumanian language article, including English language summary at end of article, and one sheet of English language bibliographic information).

Caraman et al., "Studiu Analitie Privind Constitutia Turbei Terapeutice de la Izvoarele Sucevei," *Rev. Med. Chirurg. Iasi* 479–484 (Entire Rumanian language article, including English language summary at end of article, and one sheet of English language bibliographic information).

Danysz et al., "Immunomodulatory properties of peat deriving preparation (PTT)," *Eur. J. Pharmacol.* 1990 183/3 (913–914). (Entire English language article).

Feng, "Textual Studies on the Origin of Xuanjingshi and its Identification," *Zhongcaoyao* 23:6, pp. 312–314, 1992. (Entire Chinese language article and English language bibliographic information).

Feng, "Identification of Gypsum, Anhydrite and Calcite," *Yaowu Fenxi Zazhi* 4:3, pp. 583–590, 1991. (Entire Chinese language article and English language bibliographic information).

Grimalt, et al., "Frecuencia de sensibilizacion de ciertos alergenos en pacientes afectos de tromboflebitis y/o unleras varicosas," *Med. Cut. I.L.A.* IX:415–418 (1981). (Entire Spanish language article, including English language summary at end of article).

(List continued on next page.)

*Primary Examiner*—Howard C. Lee
(74) *Attorney, Agent, or Firm*—Stoel Rives LLP

(57) ABSTRACT

Novel compositions containing at least one biologically active component derived from peat or similar composition, methods for their preparation and therapeutic uses for a variety of diseases, injuries, and conditions, including wound healing, pain, itch, inflammation, abnormal cell proliferation, or infections caused by fungal, bacterial, rickettsial or viral agents, psoriasis, allergic and other dermatitis, pruritis, eczema, actinic keratosis and similar conditions. In addition, the compositions can be used as diuretics, antiarrhythmics, and cardiac-stimulating agents, as well as for the treatment of mammalian diseases and disorders, including multiple drug resistance, cancers, asthma, rheumatoid arthritis, pain, wound healing, fungal disorders, and other inflammatory disorders. The compositions are derivable from peat or peat-related substances and may alternatively be synthetically produced.

26 Claims, 7 Drawing Sheets

U.S. PATENT DOCUMENTS

| | | |
|---|---|---|
| 4,067,714 | 1/1978 | Willard, Sr. ............... 71/24 |
| 4,067,715 | 1/1978 | Willard, Sr. ............... 71/24 |
| 4,084,938 | 4/1978 | Willard, Sr. ............... 44/1 R |
| 4,092,145 | 5/1978 | Willard, Sr. ............... 71/68 |
| 4,102,995 * | 7/1978 | Hebborn ................... 424/81 |
| 4,116,666 | 9/1978 | Willard, Sr. ............... 71/77 |
| 4,126,441 | 11/1978 | Willard, Sr. ............... 71/77 |
| 4,235,873 | 11/1980 | Packman ................... 424/47 |
| 4,272,527 | 6/1981 | Belkevich et al. ................ 424/195.1 |
| 4,370,325 | 1/1983 | Packman ................... 424/245 |
| 4,432,064 | 2/1984 | Shell et al. ............... 424/14 |
| 4,554,139 | 11/1985 | Worthington et al. ............... 423/166 |
| 4,554,151 | 11/1985 | Worthington et al. ............... 423/551 |
| 4,689,223 | 8/1987 | Arias ................... 424/154 |
| 4,735,802 | 4/1988 | Le ................... 424/154 |
| 4,943,432 | 7/1990 | Biener ................... 424/647 |
| 5,091,194 | 2/1992 | Kalso ................... 424/698 |
| 5,141,561 | 8/1992 | Ledard et al. ........................ 106/35 |
| 5,683,725 | 11/1997 | Malik et al. ........................ 424/696 |

FOREIGN PATENT DOCUMENTS

| | | |
|---|---|---|
| 3119918 | 10/1978 | (JP) . |
| 5925317 | 9/1984 | (JP) ............... A61K 9/70 |
| 2223505 | 5/1990 | (JP) ............... A61K 6/06 |
| 2300131 | 12/1990 | (JP) ............... A61K 31/575 |
| 79237 * | 5/1989 | (RO) . |
| 8600798 | 2/1986 | (WO) . |
| 8603413 | 6/1986 | (WO) . |
| 8809665 | 12/1988 | (WO) ............... A61K 33/00 |
| 9100252 | 1/1991 | (WO) ............... C04B 11/00 |
| 9111168 | 8/1991 | (WO) ............... A61K 7/16 |
| 9216216 | 10/1992 | (WO) ............... A61K 35/10 |
| 9505752 | 3/1995 | (WO) ............... A23L 1/304 |
| 9637207 | 11/1996 | (WO) ............... A61K 33/06 |

OTHER PUBLICATIONS

Itoh, "Chemistry and Pharmacological Actions of Gypsum," Jnl. Traditional Sino–Japanese Medicine 4:3, 1983. (Entire Japanese language article and English language translation of entire article).

Kostadinov et al., "Therapeutic qualities of a new Bulgarian peat preparation," Kurortol XXIV, pp. 21–27 (1987). (Entire Bulgarian language article, including English language summary at end of article, and one sheet of English language bibliographic information).

Lee et al., "Contact Dermatitis from Metal Working Fluid," Korean Journal of Dermatology 28:3 283–287 (1990) (Entire Korean language article, including English language summary at end of article, and one sheet of English language bibliographic information).

Leucuta et al., "La Formulation et: Effet Therapeutique de plusieurs Lotions antiancneiques," Clujul Medical LVIII: nr. 1, p. 72–77 (1985) (Entire French language article, incuding English language summary at end of article, and one sheet of English language bibliographic information).

Lishtvan, "Physikalisch–chemische Grundlagen des Torf–und Sapropelieneinsatzes in der Medizin," Physiother Jg. 35:3–12 (1983) (Entire German language article, including English language summary at end of article, and one sheet of English language bibliographic information).

Olivetti et al., "La Sensibilizzazione da Contatto Nelle Dermatiti da Stasi. Contributo Casistico," Chron. Derm. XV:727–734 (May 1984) (Entire Italian language article including English language summary at end of article).

Rustchev et al., "Obtaining and Investigation of Enriched Peat Used in Balneal Therapy," Kurortol XXIV, pp. 10–14 (1987) (Entire Russian language article including English language summary at end of article).

Shen, et al., "Effect of $K_2SO_4$ and $CaSO_4$ Dihydrate Solutions on Crystalization and Strength of Gypsum," J Dent Res 60:8, pp. 1410–1417 (Aug. 1981) (Entire English language article).

Trendafilova et al., "Preparation of Synthetic Gypsum $CaSO_4$ cntdot, $2H_2O$ for Medical Applications," Farmatsiya (Sofia) 41:2, pp. 6–10, 1991. (English language bibliographic information only).

Tyagi, et al., "Cell–Free Translocation of Recombinant p47–phox, a Component of the Neutrophil NADPH Oxidose: Effects of Guanosine 5'0–(3–Thiotriphosphate), Diacylglycerol, and an Anionic Amphiphile," Biochemistry 31:2765–2774 (1992). (Entire English language article).

Zhao et al., Assay of Calcium in Traditional Chinese Medicines Gypsum, Stalactite and Costazia Bone, Yaowu Fenxi Zazhi 3:5, pp. 286–288, 1983. (Entire Chinese language article and English language bibliographic information).

Feng, Yiue, "Identification of gympsum, anhydrite and calcite," YAOWU FENXI ZAZHI, 1984, vol. 4, No. 3, pp. 163–6 (English language abstract only).

Bartma'nska, J. and Schuetz, A., "The Influence of Peat Extract on the Seminiferous Epithelium of Mouse Testes," FOLIA–BIOLOGICA, 1992, 40(1–2), pp. 83–9 (English language abstract only).

Andersen, et al., "Contact allergy related to TEA–PEG–3 cocamide sulfate and cocamidopropyl betaine in shampoo," Contact Dermatitis 11(3):192–93 (1984).

Billimoria et al., "Clinical Evaluation of a New, Synthetic, Non–Steroid, Topical Agent—Bufexamac," Indian Journal of Dermatology and Venerbology 40:3 (1974).

Bracken et al., "Comparative Effectiveness of Topical Treatments for Hydrofluoric Acid Burns," Journal of Occupational Medicine 27:10 (Oct. 1985).

pg,6

Brozek B., "Physical and chemical activity of peloid cures," Fysiatr. Revmatol. Vestn. (Czechoslovakia) 59:3 145–155 (1981)ts.

Calas et al., "Epkiemiologie Des Dermatoses De Contact A Marseille," Ann Dermatol Venereol (Paris) 105:345–347 (1978).

Coenraads et al., "Susceptibility to Primary Irritants," Contact Dermatitis 1:377–381 (1975).

Gadzhieva et al., The Antibacterial Activity of a Humic Preparation Made from the Therapeutic Peat Mud of Dzalal Abad Deposit in Kirghizial, Bio–Nauki(10): 109–113, (1991) → Abstract Jun. 9, 2000.

W. Gehring, "Effects of Irritants in atopic dermatitis," Contact Dermatitis 22–292 (1990).

Gloor et al., "Wirkungseffekt Waschaktiver Substanzen in Kopfwaschmitteln," Der Hautarzt 28:404–406 (1977).

Itoh, Chemistry and Pharmacological Actions of Gypsum, Jnl. Traditional Sino–Japanese Medicine 4:3, 1983.

Lawrence et al, "Ampliative medicament allergy: concomitant sensitivity to multiple medicaments including yellow soft paraffin, white soft paraffin, gentian violet and Span 20," Contact Dermatitis 8:240–245 (1982).

Lotosh, T.D., Experimental Bases and Prospects for the Use of Humic Acid Preparations from Peat in Medicine and Agricultural Production, Bio–Nauki(10), pp. 99–103, 1991.

Lynde et al., "Patch Test results in 66 Haridressers 1973–81," *Contact Dermatitis* 8:302–307 (1982).

Marot et al., "Allergic Contact dermatitis to ethyl lactate," Contact Dermatitis 17(1):45–46 (1987).

Mesrogli et al., *Successful Prevention of Adhesions Using Peat and Humic Acids* Zentralbi–Gynakol 113(10), pp. 583–590, 1991.

Nangia et al., "Design of a new hydrocolloid dressing," Burns 15(6): 385–388 (1989).

J. Reiffers, "Contact Dermatitis to Bufexamac," Dermatologica 164:354–356 (1982).

M.M. Rieger, "Skin Irritation Physical and Chemical Considerations," *Cosmetics and Toiletries* 101:85–92 (Feb. 1986).

Shen et al., *J. Dent. Res.*, vol. 60(8), pp. 1410–1417, (1981).

Shewmake et al., "Hydrofluoric Acid Burns," *Arch Dermatol* 115:593–596 (May, 1979).

Thiel et al. "In vitro studies of the antiviral activity of ammonium humate against herpes simplex virus type 1 and type 2," Zentralbl, Bakt, Parasitenkd. Infektionsk Hyg. (Germany), pp. 304–321 (1977).

Zhorobekova et al., The Inhibition of Proteolytic Enzyme Activity by Humic Acids, Biol–Nauki (10), pp. 151–154, 1991.

Lishtvan et al., "Medical properties of peat", Int. Peat J., vol. 2: 163–178, 1987.

Kalamkaryan et al., "Physical factors in the treatment of psoriasis", Vestn. Dermatol. Venerol., vol. 0(12): 11–16, 1981.

Ye et al., "The antiinflammatory effect of Hong Yuan Peat sodium humate", Ssu–Chuan I Hsueh Yuan Hseuh Pao, vol. 16(2): 127–129, 1985.

Harrington, C. I., Low concentration dithranol and coal tar (Psorin) in psoriasis a comparison with alcoholic coal tar extract and allantoin (Alphosyl), British Journal of Clinical Practice, vol. 43(1): 27–29, Jan. 1989.

* cited by examiner

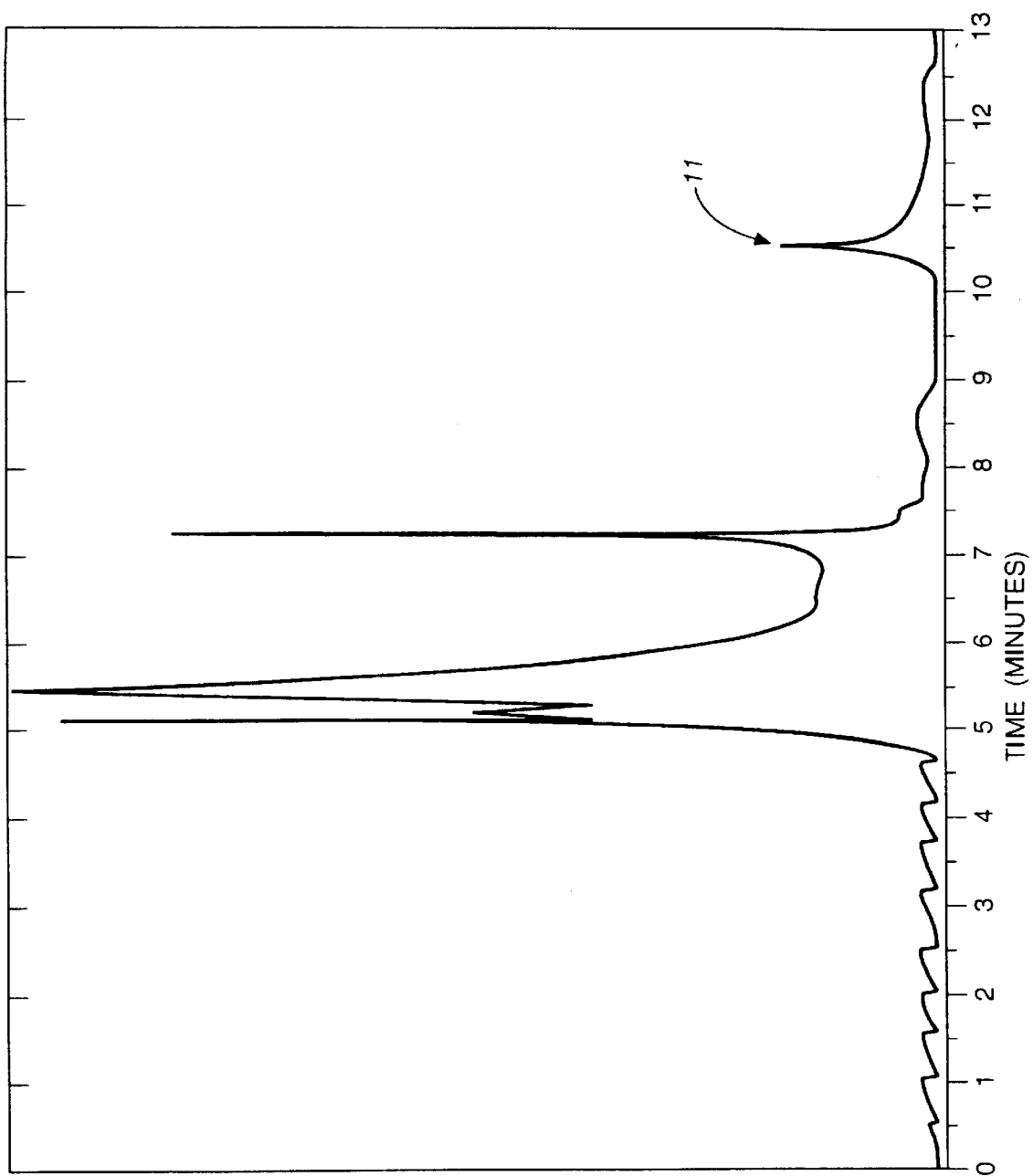
FIG._1

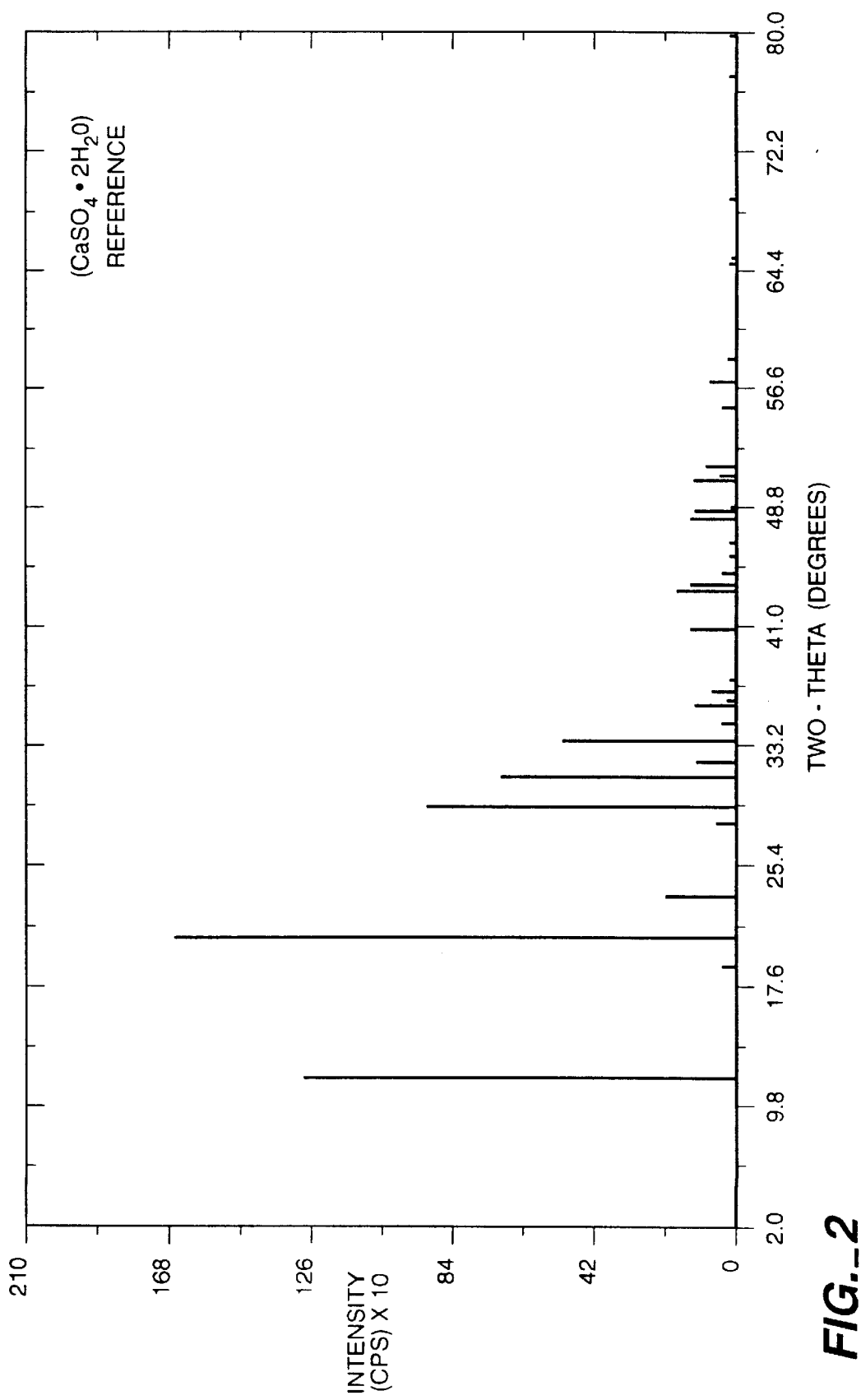
FIG._2

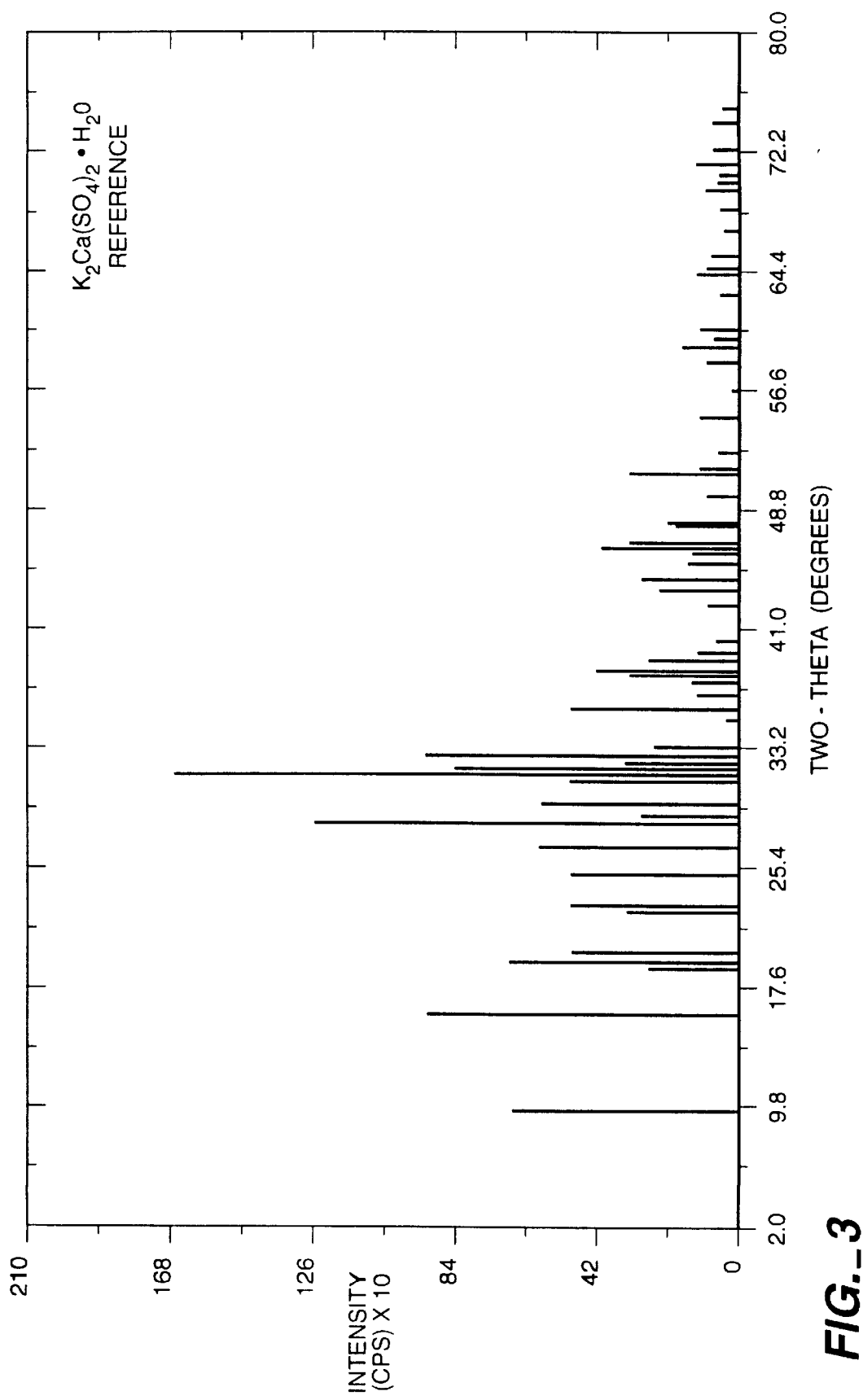
FIG._3

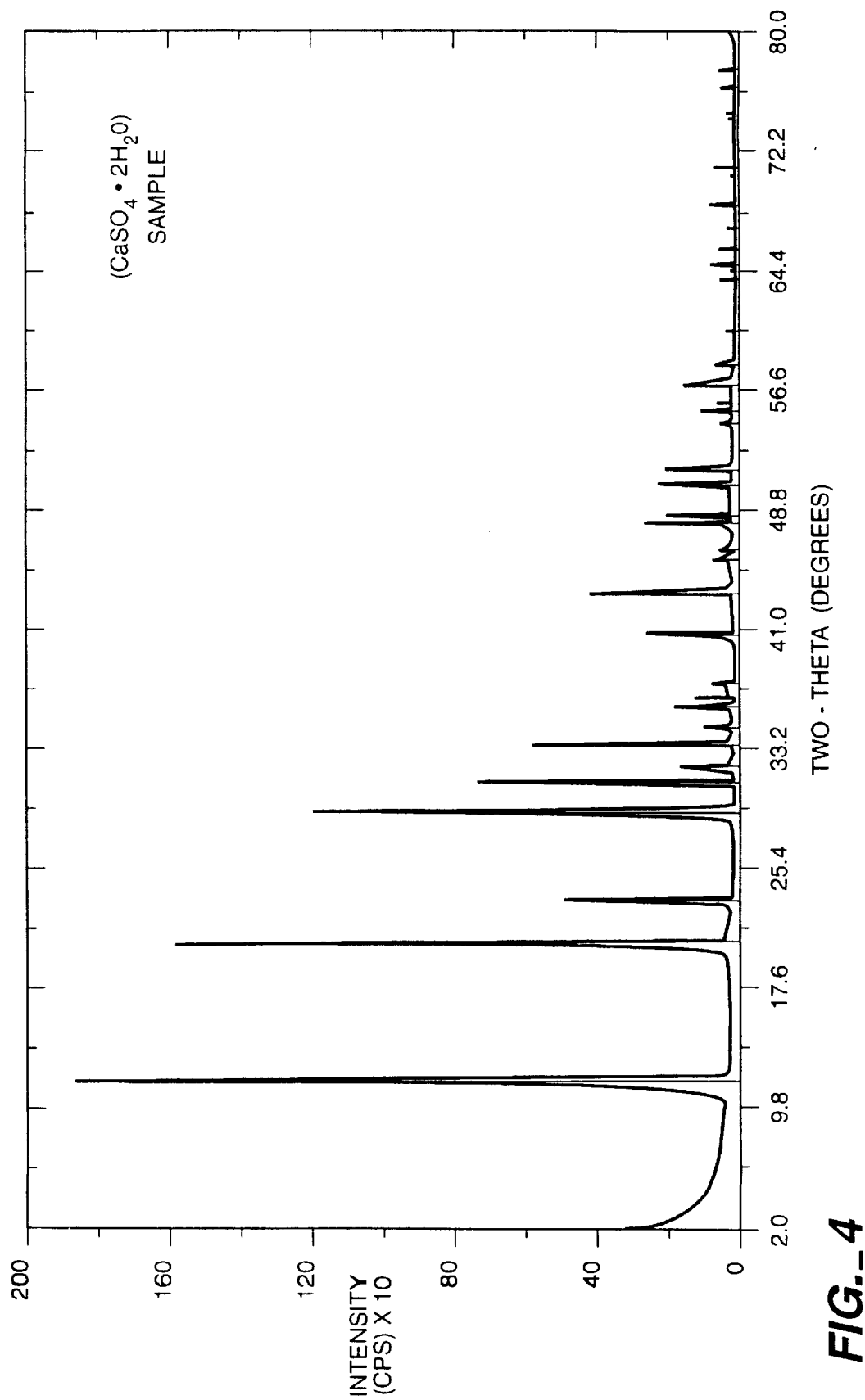
FIG._4

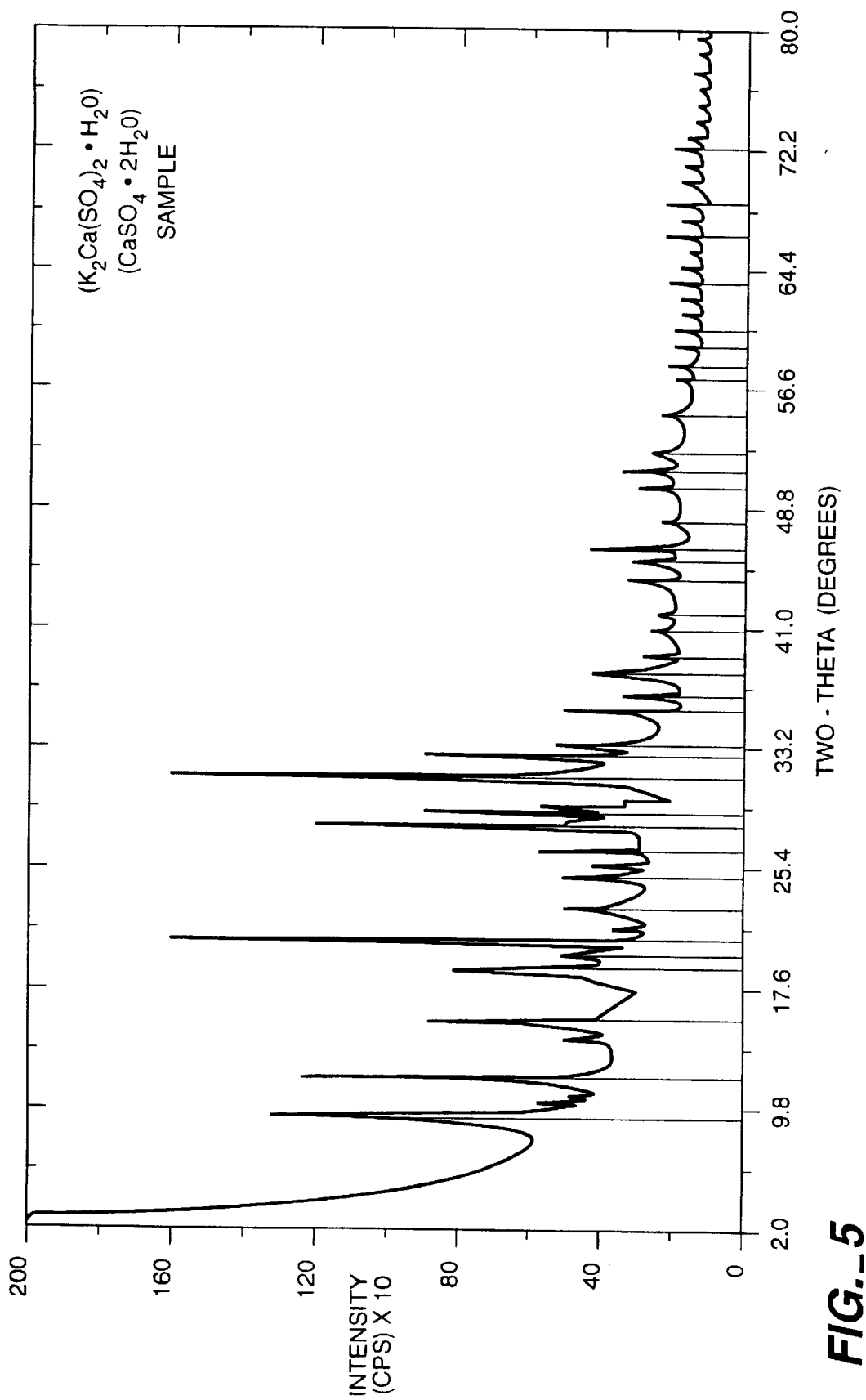
FIG._5

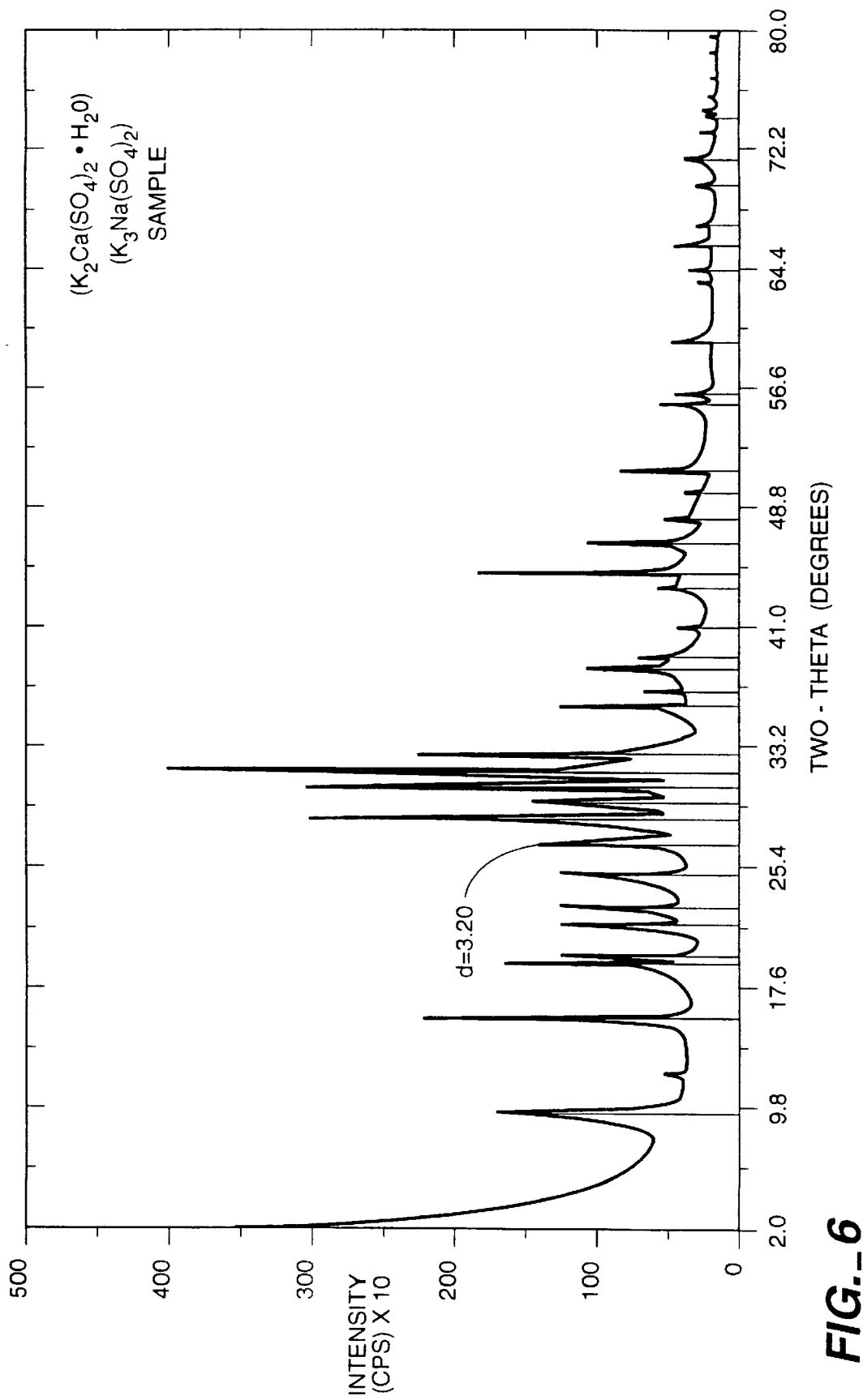
FIG._6

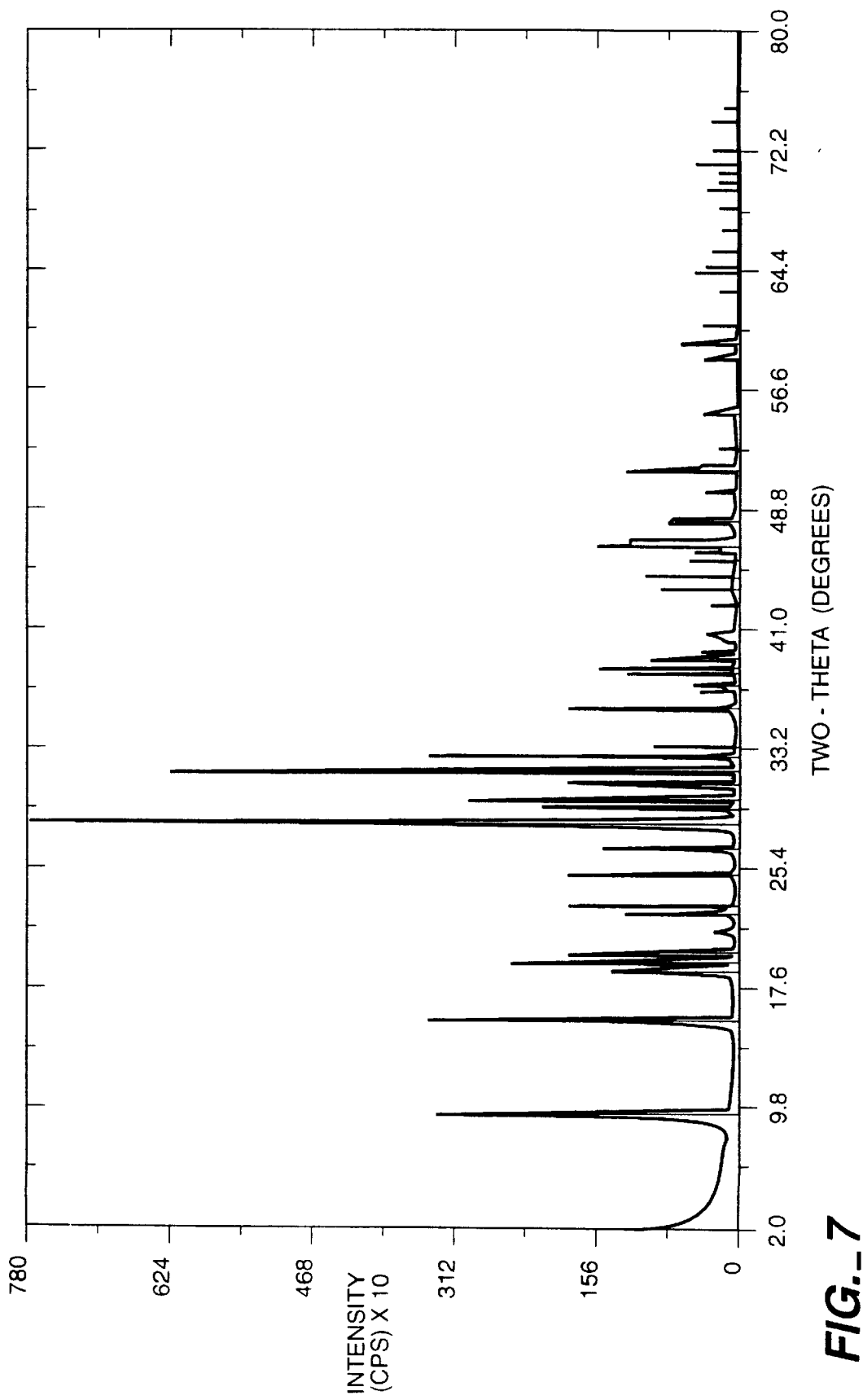
FIG._7

COMPOSITIONS AND METHODS OF TREATMENT USING PEAT DERIVATIVES

This application is a continuation of U.S. application Ser. No. 08/803,311, filed on Feb. 20, 1997, which is a continuation of U.S. application Ser. No. 08/531,099, filed on Sep. 20, 1995 abandoned, which is a continuation of U.S. application Ser. No. 08/157,987, filed on Nov. 24, 1993 abandoned, which is a continuation-in-part of U.S. application Ser. No. 07/969,793, filed on Oct. 29, 1992 abandoned, which is a continuation-in-part of U.S. application Ser. No. 07/632,020, filed on Dec. 21, 1990 abandoned.

TECHNICAL FIELD

This invention relates to novel compositions, methods of isolation and synthesis, and pharmaceutical uses of materials derived from peat. These compositions may be used for the treatment of wounds and for diseases and disorders such as pruritis, psoriasis, allergic and other dermatitis, eczema, and actinic keratosis. The compositions may be suitable for accelerating wound healing; relieving pain, itch or inflammation; reducing abnormal proliferative cell growth, particularly keratinocytes, of the skin and for hyperplastic and neoplastic conditions of other epithelial systems in the human body; and providing antifungal, antiviral, or antibacterial activity. In addition, the composition can be used as a diuretic, antiarrhythmic, and cardiac-stimulating agent. It may also be used as a therapeutic agent in the treatment of multiple drug resistance, malignancies, asthma, rheumatoid arthritis, fungal infections, and inflammatory disorders.

BACKGROUND OF THE INVENTION

Normal skin epidermis is a complex epithelial tissue containing keratinocytes that are proliferating, differentiating, and desquamating. Many common diseases of the skin epidermis, such as psoriasis, squamous cell carcinoma, keratoacanthoma, actinic keratosis, and warts, are characterized by localized abnormal proliferation and growth that is localized. For example, in psoriasis, which is characterized by scaly, red, elevated plaques on the skin, the keratinocytes are known to proliferate much more rapidly than normal. Eczema is a superficial inflammatory process involving primarily the epidermis, marked early by redness, itching, minute papules and vesicles, weeping, oozing, and crusting, and later by scaling, lichenification, and often pigmentation.

Clinical use of available treatments for diseases involving epidermal conditions is often limited by toxicity, either systemic or local. For example, methotrexate, although generally effective for treating epidermal conditions when administered orally, is rarely administered orally for fear of hepatic or bone marrow toxicity. Topical application of methotrexate has minimal or no therapeutic effect. Similarly, although topical application of 5-fluorouracil may be an effective treatment for psoriasis, it is generally considered to be unacceptably irritating. Steroid therapy, though effective, is associated with adverse side effects that are potentially so numerous or serious that prolonged use is discouraged. Photochemotherapy with psoralens and ultraviolet light, or PUVA (psoralens and UV treatment), is generally effective for treatment of epidermal conditions, but it is inconvenient to administer and causes side effects and may even cause photomutagenic and photocarcinogenic reactions.

Many of the existing treatments for wound healing and the relief of pain, itch, and inflammatory conditions, at best, are only moderately or minimally effective. Moreover, their clinical use is often limited by toxicity or undesirable side effects. Considerable research effort has been devoted to ameliorating procedures and compositions for such conditions, but few satisfactory treatments have been developed. Likewise, most therapies available for treating neoplasms and abnormal proliferative cell growth produce undesirable side effects. The compositions of the present invention are therefore directed to pharmaceutical preparations and methods for treating a variety of disorders.

In the past several years, the events that trigger the symptoms associated with hyperproliferative as well as other diseases of the skin are becoming better understood at a cellular level. By understanding the basic processes causing the symptoms of these disorders, treatments can be developed that utilize substances capable of modulating, at a cellular level, the chemical signals that lead to inflammation and cell proliferation.

One important class of chemical signals are the protein kinases, including the enzyme, protein kinase C ("PKC"). PKC is a phospholipid-dependent serine/threonine protein kinase that has a major function in cellular growth control. Protein kinases have been implicated in diseases such as psoriasis, rheumatoid arthritis, cystic fibrosis, asthma, and cancer.

PKC plays a role in the control or modulation of many metabolic and other processes. PKC is a calcium-activated phospholipid-dependent protein kinase that phosphorylates a number of intracellular protein substrates. It relays information in the form of extracellular signals across the membrane to regulate many calcium ion dependent processes.

PKC stimulates the release of phospholipase A2, which causes formation of inflammatory prostaglandins via the arachidonic acid cascade. It has been implicated as a possible intracellular "switch" (signal transducer) involved in inflammation and cell proliferation. For this reason, PKC, as well as other modulators and components of the arachidonic acid cascade, have become targets for therapeutic intervention or modulation in diseases such as psoriasis, rheumatoid arthritis, cystic fibrosis, asthma, cancer, and other inflammatory disorders.

It has been shown that psoriatic plaques have higher concentrations of PKC than normal skin. Thus, excessive PKC activity may be a causative agent of the symptoms of psoriasis.

In addition to being implicated in dermatological diseases, PKC may be involved in other disorders that are effected or regulated in some way by these enzymes. For example, the cardiac regulatory protein troponin is phosphorylated by a calcium-dependent protein kinase. Therefore, PKC modulators may have cardioregulatory activity.

PKC may further be a receptor of tumor promoters and is believed to play a critical role in the carcinogenic process. Phorbol esters and other agents promoting carcinogenesis are believed to exert their carcinogenic effects by activation of PKC, which then activates messenger-independent protein kinases such as MBP (myelin basic protein kinase) and S6P (Kemptide kinase). MBP and S6P are released from phorbol ester-stimulated cells and are believed to be activated by PKC and to be involved in carcinogenesis. They are greatly increased in phorbol ester-stimulated cells. MBP kinase is thought to serve as a central link in cellular signaling pathways in that it is activated by a variety of stimuli, e.g., growth factors, hormones and tumor promoters.

Some investigators believe that the myriad of anticarcinogenic retinoid actions can be explained by their effects as inhibitors of PKC.

There are only a few compounds with potent activity as PKC inhibitors; these include sphingosine, cyclosporine, and certain isoquinoline sulfonamides. Unfortunately, these compounds have toxic or nonspecific side effects prohibiting or limiting their use, or they are not active in vivo. Accordingly, aggressive searches continue for selective PKC modulators for use in the treatment of cancers and other inflammatory diseases, as well as other disorders that are effected by PKC activity.

Other groups of enzymes that appear to exhibit various biochemical activities are the calcium-dependent ATP'ases ("Ca-ATP'ases") and calmodulin-stimulated calcium pump ATP'ases ("calmodulin ATP'ases"). These regulators control the level of calcium ions in cells. Calcium ion concentrations are known to play an important role in both plant and animal cell regulation. Calcium is especially important in controlling constriction of muscle cells and cellular proliferation. It also plays an important role in bone metabolism and motility of spermatozoa.

Inhibitors or modulators of Ca-ATP'ases or calmodulin ATP'ases could provide important therapies for the treatment of biochemical disorders in which they play a role. There are very few known specific inhibitors of Ca-ATP'ases.

There have been claims of medicinal activities of various extracts, particularly peat wax derivatives of peat. However, none of these claims have been substantiated.

Peat is generated by the decomposition of vegetation. Peat is mainly composed of water, and the solid mass usually is only about 10 to 20 percent of the wet weight. The mass contains partially decomposed residues of dead plants combined with decaying microorganisms. Usually, peat accumulates to form a bog. The wetness and accumulated plant litter limit air access to the underlying layers of decaying vegetation. Not far below the wet surface, oxygen is virtually absent, and the decomposition can only proceed anaerobically. The term peat, as used herein, refers generally to microbial degradation products of plants, including peat and peat-derived materials, coal, and coal-derived materials. These materials include humic acids and fulvic acids, which are isolated from peat. Coal-derived material includes leonardite and lignite.

Around the world, peat has been employed for various industrial uses. In some countries such as the former Soviet Union, Finland, and Ireland, peat is primarily a fuel. In certain other countries, e.g., Germany and Finland, peat coke is produced for the metallurgical industry. In the former Soviet Union, a large, diversified peat industry produces peat-derived waxes, sugar for yeast production, and other chemicals. Peat is produced and used exclusively for horticultural purposes in the United States and Canada.

Until now, medical uses of peat derivatives have been very limited. One medicinal product made from peat is Torfot, a Soviet preparation primarily used for ophthalmic diseases. It is made by steam distillation of cotton grass-sedge peat. It contains a variety of volatile compounds including phenols, amines, and saturated carboxylic acids. Moreover, there have been reports of bactericidal and bacteriostatic fractions from reed-sedge peats. However, other investigators have been unable to confirm these activities. Attempts have been made to isolate the active material(s) responsible for these activities, mostly by acid extraction or acid degradation of peats, but no reproducible results have been obtained. Steroids have been isolated from peat; these may account for some of the previous reports of biological activities.

U.S. Pat. No. 4,272,527 claims a topical medicinal preparation containing a therapeutically effective component of an ethanol extract of peat wax resin for cure of skin diseases such as eczema and psoriasis. Crude peat wax, such as described in the latter patent, is produced when the extracting solvent is an aliphatic hydrocarbon. Peat wax is composed of a mixture of esters, acids, alcohols, and hydrocarbons derived from peat.

Unfortunately, however, peat-related compositions of therapeutic interest for the treatment of skin and other disorders have not been isolated to date and processed to an extent providing efficacious results. Therefore, there is a persisting therapeutic need for such biologically active compositions to treat skin and other disorders.

SUMMARY OF THE INVENTION

It is an object of the present invention to provide a process for preparing novel and useful compositions that are derived from peat and which possess therapeutic activities.

It is a further object of the present invention to provide peat-derived compositions, analogs, and derivatives thereof that function therapeutically by affecting, at the cellular level, signal substances such as protein kinases and ATP'ases that regulate metabolic processes.

It is yet another object of the invention to provide peat-related compositions and methods of treating a variety of diseases, including dermatologic disorders such as eczema, various allergic and other dermatitis, psoriasis and other hyperproliferative disorders, wrinkling of the skin, and wound healing and to provide compounds useful for treating inflammation, pain, and cancers and for use as antifungal agents, antiacne agents, diuretics, antiarrhythmics, and cardiac-stimulating agents.

It is yet another object of the invention to provide vetrinary therapeutics useful for the treatment of inflammations, wound healings, and allergies and as analgesics.

The mixtures and complexes forming the compositions of the present invention may be derived from natural sources, such as peat, or they may be derived synthetically. The biologically active compositions of the present invention were initially discovered in peat extracts, and considerable data relating to naturally derived peat materials has been collected.

The present invention provides active compositions obtained from peat and peat-derived materials, derivatives or synthetic analogs and synthetic counterparts thereof, methods for their production and methods for their use in the treatment of skin, inflammatory, and other disorders. The active compositions according to the present invention, are referred to herein as PAFs (Peat Active Factors). (The peat compositions of the present invention are substantially distinct in composition from prior art peat waxes or compositions derived from peat wax resins.) PAFs are isolated by extraction of peat fractions. Extraction and purification processes for producing PAF compositions that are efficacious in the treatment of various diseases are described in detail below. "PAF" is used interchangeably herein to refer to the compounds contained in the peat extract, according to this invention, or relevant fractions and their salts, and analogs and derivatives thereof.

As described in detail below, a PAF is produced by extracting peat with aqueous, organic or water-miscible organic solvents at temperatures from below room temperature to the boiling point of the solvents. The speed of extraction and total amount of product isolated are enhanced by performing the extraction at higher temperatures.

The PAFs include inorganic and organic molecules that are isolated in fractions using isolation and separation techniques known in the art based on their molecular weights. Fractions containing PAFs of a specified molecular weight range have been found useful, as described below. These fractions are referred to herein by designating "PAF" followed by the relevant molecular weight measured in daltons. The profile of the various fractions' activities may differ. According to one aspect of the present invention, the PAF may comprise an alkaline, aqueous or organic, or mixture thereof, extract of peat prepared according to the methods disclosed herein.

In one aspect, the PAF may contain novel calcium-containing and sulfate-containing compositions, and analogs and derivatives thereof, that function therapeutically or pharmaceutically in the treatment of various diseases, injuries, and disorders. Several mixtures and complexes of such calcium-containing and sulfate-containing compositions have demonstrated significant therapeutic benefits that may, but do not necessarily, include organic molecules. A first class of inorganic compositions comprises mixtures having a calcium-containing component and a sulfate-containing component, preferably calcium sulfate and potassium sulfate.

A second class of PAF compositions includes complexes of a calcium-containing or potassium-containing component and a sulfate-containing component, such as syngenite and aphthitalite. Novel methods for synthesizing high purity syngenite are also disclosed herein. The therapeutic efficacy of such calcium-containing and sulfate-containing complexes may be enhanced when combined with organic molecules of the PAF or when combined with one or more of the following elements, which may be present in elemental form, ionic form, as a salt or chelate, or in any other form: sodium; magnesium; silicon; sulfur; chlorine; potassium; strontium; zinc; copper; nickel; and manganese.

In another aspect of the present invention, organic compositions contained in the PAF that function therapeutically or pharmaceutically in the treatment of various diseases, injuries, and disorders are provided. The PAF compositions have produced therapeutic results in a variety of pharmaceuticals and applications in warm-blooded animals. These applications may be characterized generally as ameliorating conditions by promoting wound healing; alleviating pain, inflammation, and itch; and inhibiting abnormal proliferative cell growth. Additionally, such PAF compositions have demonstrated antifungal, antibacterial, and antiviral properties. The PAF compositions are also useful in cosmetic preparations.

Various delivery systems may be appropriate for administering the compositions of the present invention depending upon the condition and preferred treatment regimen. Topical delivery systems are effective and are generally preferred for most applications of the pharmaceutical composition of the present invention. Topical formulations may be produced by dissolving or combining the PAF compositions of the present invention in an aqueous or nonaqueous carrier. Suitable carriers are well known, and some are described below.

BRIEF DESCRIPTION OF THE DRAWING

FIG. 1 illustrates an elution profile of a 0.5 to 30K fraction from a peat extract purified by High Performance Liquid Chromatography ("HPLC") according the methods described herein.

FIG. 2 illustrates the X-ray powder diffraction analysis of standard gypsum published by the Joint Committee on Powder Diffraction Standards ("JCPDS") Library.

FIG. 3 illustrates the X-ray powder diffraction analysis for syngenite published by the JCPDS Library.

FIG. 4 shows an x-ray powder diffraction analysis spectrum identifying gypsum ($CaSO_4 \cdot 2H_2O$) in a peat extract sample using X-ray powder diffraction analysis.

FIG. 5 shows a spectrum identifying gypsum ($CaSO_4 \cdot 2H_2O$) and syngenite ($CaSO_4 \cdot K_2SO_4 \cdot H_2O$) in a peat extract sample using X-ray powder diffraction analysis.

FIG. 6 depicts a spectrum identifying syngenite ($CaSO_4 \cdot K_2SO_4 \cdot H_2O$) and aphthitalite ($K_3Na(SO_4)_2$) in a peat extract sample using X-ray powder diffraction analysis.

FIG. 7 illustrates an X-ray powder diffraction analysis spectrum for syngenite produced synthetically according to the methods described herein.

DETAILED DESCRIPTION OF THE PREFERRED EMBODIMENT

Peat preparations are complex mixtures containing inorganic and organic constituents that may have molecular masses ranging from less than 500 daltons to several hundred thousand or even over a million daltons. Various fractions that have been found useful according to the present invention are referred to herein according to their molecular weight or a fraction or sample number. For example, a peat extract identified as peak #11 in FIG. 1 (see Example 3) provides a high level of biochemical activity. Likewise, samples #44 and #46, described in Example 4, exhibit significant biological activity. Some of these biologically active compositions were identified by comparison of an X-ray powder diffraction spectrum of a fractionated peat extract to a standard spectrum of the Joint Committee of Powder Diffraction Standards (JCPDS) Library. The standard and experimental X-ray power diffraction spectra are illustrated in FIGS. 2–6.

All references to "components" in this application, in whatever form, are understood to include associated, dissociated, ionic, neutral, elemental, salt, hydrated, and other forms of the constituents. Thus, for example, a molecule component may be present in an associated form as a neutral or ionic species; as part of a larger complex; or in a dissociated form in which calcium and sulfate are present as distinct, noncomplex neutral or ionic species. The term "composition" also contemplates mixtures of associated, dissociated, and complex constituents.

The term "mixture," as used herein, connotes a composition wherein the constituent components are present in their associated, dissociated, elemental, ionic, salt, hydrated, and other forms. Thus, for example, a composition comprising a mixture of calcium sulfate and another sulfate-containing component, such as potassium sulfate, may comprise calcium sulfate and potassium sulfate typically not physically bonded to one another but rather in neutral or ionic forms and/or partially, substantially, or completely dissociated into their respective species. A "mixture" of two components may be substantially or entirely dissociated. It is anticipated that the precise form(s) of the individual components in a mixture will vary depending, for example, upon the relative quantity of each component, the use of aqueous or nonaqueous carriers, and the desired pharmaceutical applications or methods of treatment.

The term "complex," as used herein, connotes a composition wherein individual constituents are associated, i.e., bound to one another covalently or noncovalently as a result of hydrogen bonding or other intramolecular forces. Complexes may be present in neutral, ionic, salt, hydrated, or other forms.

All references to "calcium sulfate" herein are understood to comprehend calcium sulfate in a nonhydrated form ($CaSO_4$), as well as in hydrated forms, e.g., $CaSO_4 \cdot \frac{1}{2}H_2O$ and $CaSO_4 \cdot 2H_2O$ (commonly referred to as gypsum), unless a composition, such as gypsum, is referred to specifically.

Peat extracts may be prepared by extracting peat with aqueous solutions, organic solutions or water-miscible organic solvents at temperatures from below room temperature up to the boiling point of the solvents, but preferably below the boiling point of the solvent. Extraction at room temperature is quite suitable; however, the speed of extraction and total amount of active composition isolated are generally enhanced by carrying out the extraction treatment at elevated temperatures. Alternatively, peat may be mixed with aqueous solutions, organic solutions or a mixture of aqueous and organic solutions and allowed to stand for a period sufficient for a film to form on the surface of the mixture, preferably about one week. The film may then be reconstituted with water, to give a solution containing one or more biologically active factors.

In a preferred embodiment, the PAF compositions are derived from Bonaparte peat. Bonaparte peat is Hypnum peat obtained from Bonaparte Meadows, a peat bog near Bonaparte Lake, Washington, U.S.A. More specifically, the bog is located approximately 25 miles east of Tonasket, Wash. in Secs. 17, 20, and 29, T. 38 N., R. 30E, in eastern Okanogan County.

According to the present invention, it is preferred to use basic, aqueous solvents, particularly those containing alkali metal, alkaline earth, and ammonium hydroxides, carbonates, and bicarbonates for extraction. It is further preferred to use extracting solvents with a pH of at least 9, preferably using potassium- and sodium-containing bases. This extract is referred to as Standard Extract ("SE").

The PAF-containing solution, SE, is separated from insoluble materials by customary methods such as filtration, ultrafiltration, centrifugation, decantation, or others known to persons skilled in the art. Up to 30 percent of the dry weight of the peat goes into solution. The solution may be used directly or purified further as indicated below. Acidification of a dilute solution causes precipitation of impurities, which are discarded. If the solution SE is sufficiently concentrated, a crude mixture of solid PAF will separate after acidification to a pH of 3 or lower and may be used as such or after redissolution in an aqueous alkaline system. SE may be concentrated to dryness by lyophilization or other standard means.

Further purification of the PAFs may be performed as follows:

Salts and excess anions may be removed from the original alkaline extract, SE, by methods known to the art such as ion exclusion, ultrafiltration, etc. Materials of different molecular weights may be isolated by standard methods such as by passing through molecular sieves of appropriate materials, ultrafiltration, density gradient centrifugation, or by column, thin-layer or high-pressure liquid chromatography. The most biologically active materials are those fractions of molecular weight 10–30,000 daltons (10–30 Kd). The active compounds produced from the extraction process may occur naturally in peat, or the compounds may be a product of the extraction process.

PAFs have been demonstrated to be useful for the treatment of a wide variety of diseases and disorders. In particular, PAFs have been found to be active for the treatment of psoriasis, eczema, seborrheic keratosis, pruritis and actinic keratosis and; as an anti-inflammatory; topical analgesic; and stimulator of wound healing. In addition, it has antibacterial, antifungal, and antiviral properties and is useful in the prevention and treatment of acne, cold sores, conjunctivitis, and athlete's foot.

Veterinary uses of PAFs include use as an anti-inflammatory and analgesic and as an aid to healing of dermatitis and open wounds. In addition, PAFs are useful in treating inflammation caused by flea bites.

The PAFs of the present invention have been observed to be potent modulators of Ca-ATP'ases and other enzymes such as sodium and potassium ATP'ases and calmodulin ATP'ases. By virtue of their effect on Ca-ATP'ases, PAFs should possess diuretic activity. Because PAFs markedly increase the intracellular concentration of calcium in cells, they are anticipated to be effective for the treatment of cardiac arrhythmias, as cardiac stimulants, as tranquilizers, for treatment for osteoporosis and as antihemophilic agents.

At certain concentrations, PAFs have also been found to stimulate Mg ATP'ase. Accordingly, PAFs may be useful in the treatment of diseases or disorders in which Mg ATP'ase is involved as a regulator. PAFs have also been found to inhibit calmodulin ATP'ase. Calmodulin ATP'ase is a protein carrier of calcium, activating calcium and PDE, that is involved in many cellular functions. The PAFs of the present invention, as inhibitors of calmodulin, may be useful as antipsychotic agents and muscle relaxants and effective in the release of neurotransmitters.

PAFs have been found to be particularly effective in ameliorating the itching and plaques of psoriasis and eczema and the pain of burns and other skin wounds in humans. Although not intended to be limiting, it is hypothesized that the PAFs are active against skin diseases and other skin disorders due to their ability to inhibit or modulate the activity of PKC and related components or targets of the arachidonic acid cascade. PKC stimulates the release of phospholipase A2, which causes the formation of inflammatory prostaglandins via the arachidonic acid cascade and modulators thereof. Thus, excessive PKC activity may be a causative agent of the symptoms of psoriasis. Modulators of these arachidonic acid components and targets therefore have therapeutic activity in diseases such as psoriasis, rheumatoid arthritis, cystic fibrosis, asthma, cancer, and other inflammatory disorders.

In addition to psoriasis, PAFs may target PKC, as well as other components and modulators of the arachidonic acid cascade, providing therapeutic intervention in diseases, including multiple drug resistance, cancers, asthma, rheumatoid arthritis, and other inflammatory disorders. Therefore, it is anticipated that PAFs will be useful drugs for the treatment of these diseases.

PAFs prepared from Bonaparte peat ("BPAF") have been shown to have a particularly wide range of therapeutic uses. Such BPAFs have been found to be extremely effective for the treatment of psoriasis, eczema, and other inflammatory diseases. BPAFs also appear to stimulate the growth of cells, which makes them effective wound healers.

In addition, BPAFs have been tested and found to be active in a sheep test for cardiac stimulation and antihypertensive and diuretic activity, possibly because of their calcium ATP'ase inhibitory activity.

The PAFs of peat as described may be further fractionated, separated, or otherwise characterized to reveal active components that are also within the scope of the invention. Biologically active factors contained in the peat preparation are separated or removed from the residual solids by customary methods such as filtration, ultrafiltration, centrifugation, and decantation.

The enzyme-modulating activities of the compositions described herein also indicate the PAFs are potentially useful in diagnostics and cell-based or cell-free assay systems for research or other purposes.

The filtrate may be further purified by HPLC, preferably on a Beckman 5 micron 10 mm×25 cm C18 reversed-phase column, using a gradient of solvents starting with 100 percent methanol and ending with 100 percent deionized water, with a gradual change of proportion between the two during the interim. The flow rate is such that different compounds in the extract or solution elute at different times. Preferably, the flow rate is about 1.5 ml/min. An appropriate scanning device, preferably a UV detector set at 254 nm, is used to detect the elution of various peaks. The compounds of the solution generally are detected between 1 minute and 20 minutes, but other ranges are possible with alterations of conditions as known in the art.

Some elemental constituents present in a peat extract were identified by qualitative analysis using high resolution X-ray fluorescence spectrometry ("XRF"). The following elemental constituents were identified: sodium, magnesium, silicon, chlorine, potassium, calcium, strontium, zinc, copper, nickel, and manganese. It is believed that one or more of these elemental constituents contributes to the biological activity of peat preparations. Aluminum and sulfer may also be present in elemental form and contribute to the biological activity of the peat preparations.

Therapeutically important compositions of the present invention may also comprise a complex of organic and inorganic compounds that may, but do not necessarily, include a calcium-containing or potassium-containing component with one or more sulfate-containing components such as syngenite. Other complexes, such as $K_3Na(SO_4)_2$, may also be used. A complex of calcium sulfate may be combined with one or more other sulfate-containing components, such as syngenite, and administered in a carrier in the form of a mixture with another sulfate-containing component. Mixtures of syngenite with other sulfates, such as $MgSO_4$, $K_2SO_4$, $Al_2(SO_4)_3$, $2CaSO_4.MgSO_4.K_2SO_4.2H_2O$, $3CaO.Al_2O_3.CaSO_4.32H_2O$, $CaSO_4.Na_2SO_4$, $Na_2SO_4.10H_2O$, and $K_2SO_4.5CaSO_4$ may also be used. $K_3Na(SO_4)_2$, $NaAlSi_3O_8$, and/or $KAlSi_3O_8$ may also be incorporated in the mixtures.

The preparations of the present invention have been described above specifically with respect to compositions derived from peat. The compositions of the present invention may also be derived from other sources. For example, high-purity calcium sulfate and hydrated forms of calcium sulfate, including $CaSO_4.2H_2O$ (gypsum), $CaSO_4.\frac{1}{2}H_2O$, and the like are commercially available from a variety of sources. Potassium sulfate ($K_2SO_4$) and many of the other sulfate-containing compositions described herein are likewise commercially available. Other compositions contain identified and undefined structures or components that may not be commercially available, but are available from natural sources. For example, $K_3Na(SO_4)_2$, also known as aphthitalite, is not commercially available but may be obtained as a naturally occurring mineral or from other natural sources, i.e., peat, or it may be produced in the lab according to the protocol of Yanat'eva, O. K., et al., *Chem. Abstr.* 91 (2): 7031y (1979). Components such as $2CaSO_4.MgSO_4.K_2SO_4.2H_2O$, $3CaO.Al_2O_3.3CaSO_4.32H_2O$, $CaSO_4.Na_2SO_4$, $Na_2SO_4.10H_2O$, $NaAlSi_3O_8$, and $KAlSi_3O_8$ are not readily commercially available, but they may be obtained as naturally occurring minerals.

Syngenite ($CaSO_4.K_2SO_4.H_2O$), also referred to as the double salt of gypsum, is included in one of the preferred calcium- and sulfate-containing complexes, but it is not available commercially at high purity levels. Syngenite may be obtained as a naturally occurring mineral or from other natural sources, such as mineral deposits or peat. Applicants are aware of the two following reported syntheses for syngenite: Calistru, C., et al., *Chem. Abstr.* 106(5):31984k (1986), and Yunusova, Z., et al., *Chem. Abstr.* 114(10): 84755h (1990). They could not, however, produce high-purity syngenite according to the published methods. Applicants therefore developed the following novel protocol for synthetic production of syngenite.

Syngenite can be expediently and economically synthesized by mixing an aqueous solution of potassium sulfate with an aqueous solution of calcium sulfate. A molar excess of potassium sulfate is preferably provided to the reaction mixture. According to especially preferred embodiments, a molar access of potassium sulfate of about threefold to about tenfold is provided in the reaction mixture. A detailed protocol for syngenite synthesis is provided in Example 6. That synthetic protocol yielded pure (>90 percent) syngenite.

The preferred method for administration of the compositions of the present invention will vary according to the type and location of the disease, injury, or condition. Potentially useful methods of administration include topical application of preparation in an suitable aqueous or nonaqueous carrier, injection of the preparation in a carrier, and oral administration. The preparations may also be administered in a solid form, such as a powder or tablet. The novel compositions are preferably used topically but may be used orally or parenterally, either individually or in a pharmaceutically acceptable composition further comprising a pharmaceutically acceptable, and preferably inert, carrier or diluent. The term "pharmaceutically acceptable carriers and diluents," as used herein, contemplates any carrier or other substance that is combined with the biologically active compositions for use in any one of the enumerated methods of administration.

Suitable aqueous and nonaqueous carriers are well known in the art. In general, any liquid, cream, gel, or similar substance that does not appreciably react with the active ingredients and which is nonirritating is suitable. In a preferred embodiment, mixtures and complexes of the present invention are administered in an aqueous carrier, but various nonaqueous solvents or emulsions may also be used as carriers. Suitable carriers include, but are not limited to, 1,2,3,-trihydroxypropanol, triethanolamine, EDT, and the like. In addition, the preparations may also contain fragrances, colors, self-sterilizing agents, odor controllers, and thickeners such as natural gums and/or stabilizers.

The concentrations of biologically active constituents such as in PAF compositions may be limited by their solubility in a given pharmaceutical carrier or diluent. In such a case, the limit of solubility can be the preferred solubility. However, higher percentages of biologically active constituents may be obtained by preparing a slurry or other mixture wherein not all of the mixture or complex is in solution. For example, syngenite and/or a calcium sulfate complex, may be generally present in a pharmaceutic preparation in an amount of at least about 0.00001% to about 20%, typically about 0.001% to 2%, and preferably about 0.01% to 0.5% by weight.

The PAF compositions disclosed herein demonstrate therapeutic utility for a broad range of human and veterinary indications, including promotion of wound healing; reduction of pain, itch, and inflammation; inhibition of abnormal cell proliferation; and infections caused by fungal, bacterial, rickettsial, or viral agents. More particularly, as described in the appended examples, the PAF compositions disclosed herein have been found to be active for the treatment of skin disorders such as psoriasis and eczema, acne, seborrheic keratosis, and actinic keratosis. They are very effective in treating dermatitis, burns, and open wounds and provide pain relief from any number of conditions. The PAF compositions are also useful in the treatment of herpes, conjunctivitis, and athlete's foot.

Moreover, PAF compositions of the present invention effectively treat diseases that include multiple drug resistance, cystic fibrosis, cancers, asthma, rheumatoid arthritis, and other inflammatory disorders. Cancers for which the inventive compositions are effective include squamous cell carcinomas, epithelial carcinomas, bladder tumors, and lung tumors. The compositions of the present invention are also suitable for use in cosmetic applications.

Administration of a therapeutically effective amount of the compositions is preferably begun at the first indication of pain or other disorder and continued until symptoms disappear or cease to respond to treatment. A "therapeutically effective amount" means an amount effective to alleviate one or more symptoms or reduce or ameliorate one or more causes of the disease, injury, or disorder.

The following examples are presented for illustrative purposes only and should not be construed as limiting the invention in any way.

EXAMPLE 1

Preparation of SE

Room Temperature Extraction Process

One gram of peat recovered from Bonaparte Meadows was stirred for two hours at room temperature with 120 ml of 6 mM KOH. The mixture was centrifuged and the supernatant liquid was designated SE. Alternatively, in a scaled-up process, 1 kilogram of peat may be stirred with 12 liters of 6 mM KOH, followed by filtration to remove unwanted solids.

Elevated Temperature Extraction Process

One gram of air-dried peat was extracted by heating and stirring with 120 ml of 6 mM KOH for 20 minutes at boiling. The suspension was filtered and filtrate was referred to as Standard Boiled Extract ("SBE"). Alternatively, 1 kilogram of peat was stirred with 12 liters of 6 mM KOH for 20 minutes at boiling, followed by centrifugation to remove the solids.

EXAMPLE 2

Preparation of Purified Peat Compositions

The SBE or SE may be used "as is," but a purified preparation is desirable for many purposes and was provided using ultrafiltration techniques. Potassium hydroxide (66.4 g) was added with stirring to 88 kilos of Bonaparte peat (approximately 53 kg dry weight) suspended in 190 liters water. After 24 hours, the solids were allowed to settle. The supernatant liquid was separated by decanting or filtering. This solution corresponds to SE. Upon lyophilization, this solution has been found to yield an average of 0.4 mg/ml solids. The SE was ultrafiltered through an Amicon polysulfone 30 Kd filter, which retained material of molecular mass greater than 30,000 daltons (>30 Kd). The retained material (>30 Kd) typically contained about 0.2 mg/ml solids. The filtrate, about 130 liters, contained materials of molecular mass <30 Kd and contained an average of about 0.2 mg/ml solids. A 25 liter portion of this <30 Kd solution was ultrafiltered through another Amicon filter that retained materials of molecular mass greater than 10 Kd to give 250 ml of a retentate containing an average of 0.1 mg/ml solids.

The filtrate of the 10K treatment was ultrafiltered through a 2K Amicon filter to give a retentate containing 0.2 mg/kg PAF of 2–10,000 daltons (PAF 2–10K). The filtrate was ultrafiltered through an Amicon 0.50 filter to give a retentate containing PAF material of molecular weight 500 to 1,000 daltons (PAF 0.5–2K).

PAF can be isolated by a similar procedure from other peats and coal sources, including humic and fulvic acids, leonardite, and lignite.

EXAMPLE 3

Preparation of Highly Purified Peat Composition

Peat was extracted, purified by ultrafiltration, and then further purified using HPLC. To prepare a standard extract, 65 kilograms of peat and 264 grams of KOH were stirred in 760 liters of water. After 24 hours, the solids were allowed to settle. The supernatant liquid was filtered or decanted to produce the SE.

The SE was ultrafiltered through an Amicon hollow filter cartridge 30 Kd to yield a filtrate comprising 740 liters containing material of molecular mass <30 Kd.

Although filtrates have been prepared using different size exclusion methods, all <30 Kd fractions have been found enriched in materials having desirable biological properties. Peat preparations comprising the <30 Kd fraction may be further resolved by processing on a 0.5 Kd Amicon spiral wound cartridge, which retains material having a molecular mass from 0.5–30 Kd that is suitable for HPLC. The HPLC fraction was obtained by injecting a 250 ul portion of a 0.5–30 Kd extract onto a Beckman 5 micron 10 mm×25 cm C-18 (reversed-phase) High Pressure Liquid Chromatography column. A gradient of solvents beginning with methanol (100 percent) and gradually changing to end with deionized water (100 percent) was passed through the column at a flow rate of 1.5 ml/min. The eluate was scanned by a UV detector set at a wavelength 254 nm.

A fraction referred to as peak #11 contains a high concentration of biologically active material. Peak #11 eluted from 9 to 11 minutes in the HPLC system described above. FIG. 1 illustrates the HPLC results and identifies peak #11. X-ray powder diffraction analysis identifies compounds in peak #11 as gypsum ($CaSO_4 \cdot 2H_2O$), syngenite ($CaSO_4 \cdot K_2SO_4 \cdot H_2O$), and aphthitalite ($K_3Na(SO_4)_2$). FIGS. 2 and 3 illustrate the x-ray powder diffraction standard spectra for gypsum and syngenite, respectively, published by the JCPDS Library. FIGS. 4 and 5 illustrate spectra identifying gypsum (FIG. 4) and both gypsum and syngenite (FIG. 5) in the peat sample. FIG. 6 illustrates a spectrum identifying both syngenite and aphthitalite in a peak #11 peat sample. Further research are expected to demonstrate that organic compositions are also significant compositions in peak #11.

EXAMPLE 4

Alternate Peat Purification Preparation

An aqueous solution of peat was prepared and allowed to stand unfiltered for a time period sufficient for a film to form on the surface, usually at least one week.

The film was carefully skimmed from the surface and mixed with water. The resulting film solution was ultrafiltered through a 1 Kd Amicon spiral wound cartridge to dryness, and the >1 Kd fraction was discarded. The solution <1 Kd was then filtered through an Amicon spiral wound cartridge with a nominal <0.5 Kd exclusion. The retentate was lyophilized to dryness, reconstituted in water, and called sample #44. The filtrate of <0.5 Kd was concentrated by lyophilization and called sample #46.

Samples #44 and #46 yield fractions with the same HPLC retention times as peak #11 from the SE and a similar proportion of calcium sulfate (gypsum) as the major aspect of their chemical compositions. Sample #46, when repurified by HPLC, eluted as a single peak that comprised two compounds, of which syngenite was a major component. Recent research shows that organic molecules also comprise another major component.

EXAMPLE 5

Application of Peat Preparation to Human Patients

Numerous human trials were conducted to demonstrate the utility and effectiveness of treatments using the inorganic compositions of the present invention. The inorganic compositions administered to humans patients in the following studies were derived from natural peat sources, unless otherwise indicated. The peat preparation administered to human patients was isolated from Bonaparte peat and purified as set forth in Example 2. Unless otherwise indicated, an aqueous 0.2 percent solution by weight of the 10–30 Kd peat preparation ("peat preparation") was applied topically three times a day. Other peat fractions, including a 3–30 Kd fraction of standard extract, peak #11, and/or samples #44 and #46 were applied topically two and occasionally three times daily in a liquid carrier in the trials indicated. Aqueous and emollient peat preparations were administered.

Psoriasis—Patients 1 Through 5

Studies were carried out on human patients 1 through 5 having long-standing psoriasis and for whom conventional therapy gave only poor-to-moderate control. All other treatments were discontinued, except for one patient who used Diprolene cream on one elbow for comparison and another patient who continued her usual twice-weekly UVB treatments. The 10–30 Kd peat preparation was applied topically twice daily to the involved sites. The results are shown in Table 1.

The 10–30 Kd peat preparation was well tolerated without irritation or staining. Smaller, more recent, and less thick plaques showed early improvement, i.e., within two weeks. The psoriasis plaques were less responsive when chronic and well established. The improvement in erythema and scale of the psoriasis plaques was seen in three of the five patients, and improvement in scales was seen in four of the five patients. One patient had complete clearing of all his plaques except for a small residual area on the elbow. The 10–30 Kd peat extract was equal in efficacy to a potent steroid applied topically.

Pruritus/Cutaneous Pain—Patients 6 Through 11

Patients 6 through 11 had nonurticarial conditions. This category is exclusive of those with pruritive eczema or xerosis. One patient had post-scabetic pruritus. One had persistent scrotal idiopathic pruritus that was poorly controlled with topical steroids. Two had chronic pruritic nodularis. One had severe pruritus/cutaneous pain secondary to hepatic sarcoma. One had intense pruritus over the graft and keloidal area resulting from third-degree burns over 40 percent of her body.

None of the patients, except the post-scabetic patient, were controlled with oral H-1 and H-2 antagonists either alone or in combination (e.g., Seldane™ (terfenadine) and Zantac™ (ranitidine) or doxepin alone). Application of the following topical agents did not produce satisfactory results: Prame Gel lotion, Zostrix™ (capsaicin), category 1 or 2 corticosteroid creams where appropriate, and nonfluorinated corticosteroids on the scrotum.

Upon application of a peat preparation comprising 3–30 Kd peat preparation and peak #11, there was immediate relief of the pruritus. The pruritic nodularis patients reduced their excoriation to a minimal level. The post-scabetic pruritus cleared over a week, but again relief was immediate. The previously unresponsive scrotal pruritus was completely relieved but required two or three weeks of treatment to obtain resolution. The healed third-degree burn patient had immediate relief and required six to eight applications a day to maintain relief. This intense application was not feasible on a continued basis and thus quick, but not lasting, relief was obtained in this instance. The hepatic sarcoma patient was in her last two months of life and her continuous itching and pain were so severe that normal sleep and daily functioning were not possible. In this case, she had not responded to the above-noted oral agents or Axsain cream. Application of the peat preparation produced an immediate improvement of both the itch and the deep, burning pain sensation. She required four applications daily but no longer dug at her skin and was able to sleep.

TABLE 1

Results of Treatments with Purified Peat Preparation

| | Week of Treatment | | | | | | | | | | | | | | |
|---|---|---|---|---|---|---|---|---|---|---|---|---|---|---|---|
| | 1 | | | 2 | | | 3 | | | 4 | | | 5 | | |
| | W | NC | I | W | NC | I | W | NC | I | W | NC | I | W | NC | I |
| SCALING | 0 | 3 | 2 | 0 | 3 | 2 | 0 | 2 | 3 | 0 | 1 | 4 | 0 | 1 | 4* |
| ERYTHEMA | 0 | 3 | 2 | 0 | 3 | 2 | 0 | 2 | 3 | 0 | 1 | 4 | 0 | 2 | 3 |
| THICKNESS | 0 | 3 | 2 | 0 | 3 | 2 | 0 | 2 | 3 | 0 | 2 | 3 | 0 | 2 | 3 |

W: Worse
NC: No change
I: Improved
*Complete clearing in one patient

Vesicular Hand/Foot Dermatitis—Patients 12 Through 14

Human patients 12 through 14 were treated with a preparation comprising peak #11. In all cases, one pruritus was relieved immediately, but the vesicular-pustular component was not controlled. Two of the patients required systemic corticosteroids and either Ultravate™ (halobetasol propionate) or Temovate™ (clobetasol propionate) ointment for control. The third evolved into pustular psoriasis and is now using PUVA.

Atopic Dermatitis—Patients 15 Through 20

Human patients 15 through 20 having chronic atopic dermatitis of the face were treated with 10–30 Kd peat preparation. All were experiencing intense pruritus of the dry facial eczema along with increasing lichenification resulting from the rubbing and inflammation. One also had similar severity in his hands and arms along with excoriation. In addition to the emollients, all were using either Locoid™ (hydrocortisone butyrate) or Elocon™ (mometasone furoate) cream twice daily on the facial eczema. All were showing signs of steroid atrophy.

The relief of the pruritus was immediate, and the dermatitis cleared over four to five days. Remission of several weeks was observed in two patients, and the conditions of three were eventually maintained with one daily application. One patient was completely cleared of active dermatitis and continued treatment for several months. After a three-week hiatus, treatment was resumed, but without the same response. This patient could not fully control the condition solely using a composition comprising peak #11. Twice weekly Locoid™ cream was required along with daily administration of peat extract to control the pruritic dermatitis.

Dental Application—Patient 21

Patient 21 had four wisdom teeth extracted. Two of the teeth were seriously impacted. The patient was given a prescription for hydrocodone, a narcotic analgesic, and released. The patient was in a great deal of pain, and, instead of taking the hydrocodone, he swished a few milliliters of a solution comprising peak #11 around in his mouth. The pain was relieved instantaneously. The patient repeated the administration at 30-minute intervals for about two hours. Administration at two-hour intervals seemed to be sufficient thereafter. This patient continued with this schedule for approximately two days and was essentially pain-free.

Burn—Patient 22

Patient 22 sustained second- and third-degree burns over most of three fingers on her right hand. The burns were caused by contact with a flame and with burning nylon. The emergency room doctor diagnosed the burns, cut away the burned nylon and skin, and applied sulfadiazine. The sulfadiazine was later removed and a 3–30 Kd peat preparation was applied. The patient dressed the wound at least twice daily with bandages soaked with the 3–30 Kd peat preparation. The pain abated almost immediately upon application of the preparation and the wounds remained largely pain-free. Within three weeks, the patient's fingers were healed but still pink. After two more weeks, there were no indications of scars or wound marks of any sort; the skin of the fingers appeared healthy in all respects.

Pain and Lesions—Patient 23

Patient 23 had a laminectomy and subsequently experienced spasms in his lower back. After eight months, the patient was treated with a 10–30 Kd peat preparation in a cream carrier, and he was immediately relieved of pain. Patient 23 also has a long-standing problem with his feet that was reported to be jungle rot and that caused unbearable itching and open lesions. After applying the 10–30 Kd purified peat preparation cream to his feet, the pain and itching subsided and the odor disappeared.

Chronic Arthritis—Patient 24

Patient 24 had suffered from chronic arthritis for about 12 years and consulted several doctors and chiropractors over the years. Patient 24 was treated with various oral drugs and injections of cortisone, but none of these treatments provided relief. Patient 24 applied a 3–30 Kd peat preparation topically to his inflamed foot, knee, and shoulder twice daily. Within five days, there was significant relief in all areas. Patient 24 was able to discontinue use of the preparation after about 10 days.

Eczema—Patients 25 Through 29

Patient 25 had eczema for approximately eight years. He had been unresponsive to other antieczema therapy, and the eczema had never completely disappeared or been effectively treated. He applied a solution comprising 10–30 Kd peat preparation (2 mg/ml) diluted with 15 ml water and 15 ml of a 0.004 percent solution of calcium gluconate (final pH 7.3) to well-established spots of eczema. Skin irritation (burning), thought to be caused by the calcium gluconate, occurred for approximately 30 minutes. Applications were continued twice daily for about 10 days. The affected area became quite red; however, all lesions disappeared within eight days. The redness disappeared after treatment with Lidex cream for two days, leaving only slight discoloration of the skin. No lesions have reappeared in the same locations, but the eczema continued to appear in different locations. The new eczema spots were treated with a peat preparation that contained no calcium gluconate. These treatments produced positive results.

Patient 26 applied a 10–30 Kd peat preparation to eczema covering both legs between his ankles and knees. Itching was so severe when the patient was in contact with warm or hot water that taking a shower was almost unbearable. Administering the preparation before a shower greatly reduced itching; used afterward, the preparation stopped the itching within two minutes.

Patient 27 had very difficult eczema over one-third of her body. She treated one arm with a 3–30 Kd peat preparation and used the other arm as a control. The treated arm became clear, whereas the control arm had 25 percent coverage of eczema. Patient 27 also administered the preparation on her face, and it eliminated the pain associated with the eczema on her face less than 15 seconds after application. Steroids were less effective.

Patient 28 had mild eczema that could be controlled with steroids, using lengthy treatments. Upon application of a 3–30 Kd peat preparation, he was free from lesions after seven days.

Patient 29 had a large amount of eczema on her face. After applying a 10–30 Kd peat preparation twice daily for one week, her face was cleared of all eczema. She continued treatment once daily for another three weeks. The eczema had not reemerged after two months.

Wound Healing—Patients 30 and 31

Patient 30 applied a 10–30 Kd peat preparation to sores from abrasions. One of these sores was infected to the point that it was oozing and weeping. Within two to three days of treatment with the preparation, the redness and infection were completely gone and complete healing occurred. This healing occurred as soon, if not sooner, as another untreated sore that did not have any apparent infection.

Patient 31 had open and bleeding sores on his hands caused by involuntary scratching of eczema during the night. Cortisone injections controlled the itching for about four to six weeks, but the patient was only able to take cortisone shots twice a year. After two days of treatment with a 10–30 Kd peat preparation, the itching stopped and healing began. After seven days, the eczema was completely controlled. When application of the preparation was discontinued, the eczema returned, but to a lesser degree. Following six days of renewed treatment, the eczema once again disappeared. Patient 31 continued treatment with the preparation for eight months with effective control of his eczema. No side effects were observed.

Psoriasis—Patients 32 and 33

Patient 32 had suffered from psoriasis on his arms and elbows for over 10 years. A 10–30 Kd peat preparation was applied to one elbow twice daily for approximately nine months, with the occasional simultaneous application of fluocinonide cream. Fluocinonide cream alone was used on the other elbow.

The elbow treated with the fluocinonide alone evidenced only subsided flaking of the skin, but no decrease in the skin lesions. The patient observed significant improvement within one week by using the preparation combined with the occasional application of fluocinonide cream. Flaking and itching had stopped, and the lesions on his skin were reduced in size. Hair started growing in these areas. Patient 32 also applied the preparation to open wounds, such as minor cuts, and observed good healing effects without infection.

Patient 33 had psoriasis that seemed to only manifest itself after an occurrence of strep throat. Her only successful treatment had been with chemotherapeutic agents. Application of a 10–30 Kd peat preparation cleared up the treated psoriatic area in two to three weeks.

Epidermal Conditions—Patients 34 Through 44

During the winter months, Patient 34 had an extreme case of dry skin and a red rash on the inside of her legs. The itching immediately ceased upon application of the 10–30 Kd peat preparation. Within one week, the red rash was gone and the dry skin was completely normal.

Patient 35 applied a 10–30 Kd peat preparation to treat sumac poisoning on his legs and arms. He had previously used a 1 percent cortisone treatment to soothe the burning and itching and to clear up the blisters, which took seven to 10 days. Before treatment, the skin would turn red and peel like a sunburn before the irritation would stop. After applying the preparation, he had immediate relief from the burning and itching. Within 24 hours the blisters were gone, and within 48 hours the redness was gone and the skin looked normal.

Patient 36 applied a 10–30 Kd peat preparation to her lip at the first sign of a cold sore. The preparation stopped the lesion from appearing. There was no pain after the first application.

Patient 37 experienced mouth sores from overuse of ibuprofen. A 10–30 Kd peat preparation was applied directly to the sores and cured the condition in 12 hours. The healing process generally took three to five days if untreated. Patient 37 also applied the preparation to numerous cuts and abrasions to effectively avoid infection and accelerate the healing process. Pain was generally controlled within five seconds after application.

Patient 38 had boil-like swelling as a result of a lingering staphylococcal infection. The condition generally resulted in an infection that required lancing. After application of a 10–30 Kd peat preparation to the affected areas three or four times daily for five days, the condition completely healed. Patient 38 also applied the preparation to skin blemishes with excellent results. Patient 39 treated a third-degree kitchen stove burn with a 10–30 Kd peat preparation 10 minutes after sustaining the burn. The associated pain diminished within 15 seconds.

Patient 40 applied a 10–30 Kd peat preparation to her leg about 24 hours after it was burned. At the time she applied the preparation, the burn was quite painful and had blistered. Immediately after treatment, the pain subsided. Within 24 hours, the blistering was gone and the burned skin was smooth.

Two hours after Patient 41 burned his finger, it was blistered and weeping. After applying a 10–30 Kd peat preparation, he experienced immediate relief. The blistering was gone overnight. Patient 41 also applied the preparation to a finger inflamed by a steel sliver, and there was an immediate reduction in pain and pressure.

Patient 42 experienced itching in his right eye. After one day, his eye became red and inflamed. Flushing with eyewash did not provide relief. After several days, the eye was completely sealed shut and very swollen and red, and the patient was diagnosed with conjunctivitis. The patient applied a cotton pad soaked with a 10–30 Kd peat preparation. On the following day, the patient had very little swelling and no pain in his eye, but the eye was still red. He again applied a cotton pad soaked with the preparation before going to bed. On the following day, the eye had no swelling, pain, or itching. Two days later, the eye was completely healed.

Patient 43 applied a 10–30 Kd peat preparation to portions of a badly skinned knee. Within two days, all of the soreness and redness was gone and a thin-layer scab formed. The untreated area was still sore to the touch. The scab that formed on the treated area was much thinner than that of the untreated area. There was no pus at any time on the treated area, but there was a continuing secretion of pus for five days on the untreated area. The subject reported that overall healing of the treated wound was at least twice as fast as usual.

Patient 44 had acne congolbata on his back, buttocks, and legs. This is a severe, painful condition of boils that must be frequently lanced. He was being treated with Prednisone at a dose of 27 mg a day. This treatment barely contained the boils. The patient was visiting the emergency room at the hospital as much as once a week for lancing. He began using 60 mgs/250 ml of peat preparation #44 in a cream. He was able to reduce the dose of Prednisone to 5 mg a day, with continued reduction of the Prednisone dose thereafter. With continuing treatment, the boils stopped erupting and the pain diminished.

Fungal Condition—Patient 45

Patient 45 suffered from a chronic athlete's foot infection. He had been told by physicians that his condition was incurable. After one application of a 10–30 Kd peat preparation, his condition began to clear. After the second and third applications, there was no evidence of the fungal infection.

Shingles—Patient 46

Two children were diagnosed with shingles. A prescribed medication was used on them for three weeks with no relief. Peat preparation #44 was administered topically and provided immediate relief from the pain. In two days, the lesions were gone.

EXAMPLE 6

Mixtures and Complexes

Inorganic composition mixtures and/or compositions of complexes included in the present invention were also synthesized and administered to human patients. Inorganic mixtures were prepared using a combination of gypsum ($CaSO_4.2H_2O$) and potassium sulfate ($K_2SO_4$). More specifically, a "mixture" containing 0.6 mg of equimolar $CaSO_4.2H_2O$ and $K_2SO_4$ in a carrier comprising 2 ml of ethanamine-N-N-diethyl-trifluoroacetate ("EDT") and glycerol in a 1:1 ratio was formulated.

Patients 47 and 48 applied the mixture to small, 0.5 to 1.0 $cm^2$ acid burns. The mixture totally relieved pain within three to seven minutes after a single application. Treatment with a water placebo on some sites yielded no pain relief. Treatment with a 3–30 Kd peat preparation yielded temporary pain relief after about four minutes, but additional treatments were required to sustain pain relief.

Patient 49 applied the mixture topically to treat long-term lower back pain due to nerve damage caused by disc deterioration. Pain relief occurred within seconds and was sustained.

EXAMPLE 7

Synthesis of Syngenite

Syngenite was synthesized according to the following protocol. Solution A was formulated by dissolving 125 moles of $K_2SO_4$ in distilled water (450 ml) at room temperature. Solution B was formulated by mixing 2.5 moles $CaSO_4$ in distilled water (50 ml) at room temperature with constant stirring. Solution A was slowly poured into solution B with constant stirring. The reaction mixture was maintained for four hours at an isotherm of 38° C.

Upon evaporation of water, crystals formed that were filtered through a membrane filter. The crystals were washed with a small amount of ice-cold water and methanol (at a 1:1 ratio), then with ice-cold water alone, and then they were dried. The crystals thus obtained were recrystallized with water, resulting in the formation of pure (>90 percent) syngenite.

EXAMPLE 8

Comparative Studies

Experiments were conducted to compare the effectiveness of samples #44 and #46 to peak #11. Based upon the reports of the test subject, samples #44 and #46 both worked about 30 percent as well as peak #11. When samples #44 and #46 were administered in an EDT carrier, however, each sample produced results comparable to those obtained with peak #11.

Another patient topically administered three different preparations to an area of pain. The three preparations included (1) a 3–30 Kd peat preparation, (2) a peak #11 preparation in a cream, and (3) an equimolar mixture of $CaSO_4.2H_2O$ and $K_2SO_4$ (each about 0.03 percent by weight) in 1,2,3-trihydroxypropanol. The preparations were applied to different areas to reduce intense pain associated with a chronic arthritic condition of many years' duration.

The patient reported that the 3–30 Kd peat preparation produced noticeable but short-lived relief for 20 minutes, with some relief lasting for approximately one hour. He also reported that the peak #11 preparation provided substantial relief for 20 minutes after application, coupled with reduced relief for three to four hours. The patient also reported that the use of the mixture in the 1,2,3-trihydroxypropanol carrier produced relief equivalent to the peak #11 and had the additional advantage that it was neither greasy nor sticky.

EXAMPLE 9

Additional Comparative Studies

Three subjects, two suffering lower back pain and one with pain due to peripheral neuritis of the lower extremities, were each given four blinded samples for uniform-dose topical application. They were instructed to first apply sample #1 and then five minutes later to record the level of pain relief according to the following scale: No Relief=0 percent, Minor Relief=33 percent, Significant Relief=66 percent, and Complete Relief=100 percent. If No Relief or Minor Relief were noted, subjects were instructed to apply sample #2 to a new area of pain. The same general scheme was continued until all four samples had been tested. The results of the test were as follows:

| | Subjects' Responses | | | | |
|---|---|---|---|---|---|
| Sample No. | Complete | Significant | Minor | No Relief | Duration |
| #1 | 3/3 | | | | 1–4* hrs |
| #2 | | 1/3 | 2/3 | | 3 hours |
| #3 | | | 1/3 | 2/3 | |
| #4 | | | | 3/3 | |

The small size of this group permits only one clear conclusion. Sample #1 provided clear analgesic benefit for all subjects compared to the other samples. The composition of sample #1 was 0.25 percent $CaSO_4.2H_2O$ plus 0.05 percent syngenite in UNIBASE cream. UNIBASE is a commercially available topical cream. The composition of samples #2, #3, and #4, respectively, was as follows: #2=UNIBASE alone, #3=0.25 percent syngenite in UNIBASE, and #4=0.25 percent $CaSO_4.K_2SO_4.H_2O$ in UNIBASE. In the subject with pain due to neuritis there was also a very significant level of local inflammation that was virtually completely ameliorated by the application of sample #1.

This example demonstrates several important aspects of the invention. First, it utilized syngenite prepared by the claimed new synthetic process. Second, it showed that a formulation composed of calcium sulfate and another sulfate-containing compound (syngenite) is responsible for the amelioration of pain and inflammation in human subjects. Third, because both of these compounds are known to be part of the 3–30 Kd, 10–30 Kd, and #11, #44, and #46 fractions in variable proportions, we can conclude that at least some of the beneficial results produced by these preparations are due to the presence of these components.

EXAMPLE 10

Veterinary Applications

The inorganic compositions of the present invention also demonstrate significant utility for veterinary applications. The results of several animal experiments are discussed below.

Animal subject A was a dog that started intense scratching after a visit to the seashore. After two to five days, itching increased with some hair loss as a result of continued scratching. On day six, the dog was sprayed with flea and tick powder but showed no improvement. The bites continued to worsen and soon secreted a pus-like substance. The dog was treated by applying a 10–30 Kd peat preparation in spray form. The spray was re-applied eight hours later. On the following day, there was no pus and less scratching. The preparation was reapplied three times during the day, and the bites were smaller and less red. After one more day of treatment, the bites were smaller in size and were only pink in color, and there was no scratching.

Animal subject B was a racehorse suffering from sores on its legs. The horse was diagnosed as being allergic to mud and was treated with triamcinolone 0.1 percent acetonide cream. He had scabbing and oozing of pus on his legs and was sore and stiff. There was no improvement after four months of treatment under veterinary supervision. A 10–30 Kd peat preparation was sprayed directly on the horse's legs once a day. After three days, healing was noted. After one week, the infected areas were healed, and the horse's hair was growing back.

Animal subject C was a large dog that had had serious eczema and dry skin since birth. Numerous sprays, powders, shampoos, pills, and injections were administered without success. After spraying the dog with a 10–30 Kd peat preparation for two weeks, itching was resolved and there was less flaking and dry skin.

Animal subjects D and E were adult Labrador Retrievers infested with fleas. A 10–30 Kd peat preparation was applied in a liquid form three to four times daily to the thighs, perianal region, and tail of the two dogs. No other attempt was made to treat the fleas on the dogs or in their environment. Before treatment, bitten fur and a flea-induced dermatitis were obvious. An immediate reduction in biting, scratching, and licking of the involved sites was apparent upon initial application of the preparation. Because the flea population was not reduced, four daily treatments were required to control the pruritus and to clear the dermatitis.

Animal subject F, a German Shorthair dog, was treated with the 10–30 Kd peat preparation for a nonflea-associated, nonspecific dermatitis. Applications were inconsistent and usually twice daily. There was a noticeable reduction in the scratching and dermatitis within one week.

An open clinical trial was conducted in an attempt to determine the efficacy of a 10–30 Kd peat preparation when topically applied for treating a variety of itching canine skin diseases. Most of the dogs suffered from allergy-associated itch (flea bite, inhalation, and/or food allergies). In the more than 50 dogs evaluated, the preparation was instrumental in the relief of itch in over 50 percent of the subjects. No adverse side effects were noted. Itch relief was usually noted within three days of initiating therapy. Additionally, the preparation demonstrated significant antiinflammatory properties (rapid decreases in erythema and swelling) when applied to allergy-associated rashes. Preparations comprising syngenite produced synthetically according to the protocol given in Example 7 produced similar therapeutic results when administered to dogs.

EXAMPLE 11

Treatment of Bovine Squamous Cell Carcinoma

Bovine ocular squamous cell carcinoma in cattle is a common neoplasm of the bovine eye and adenexa. Squamous cell carcinomas may also affect other species of animals. Bovine ocular squamous cell carcinoma is best known by its colloquial name of cancer-eye. The initial lesion may be on the eyelid or any structure in the conjunctival sac except the vascular cornea or the pigmented eyelid. The lesion develops in three stages. The first stage is the formation of a plaque, the second stage is formation of a papilloma, and the third stage is the squamous cell carcinoma.

The first two stages are nonmalignant and have up to an 88 percent regression rate. The third stage is malignant and does not regress. These carcinomas develop most commonly on the nictitating membrane, the eyelids, and the corneal limbus. They grow rapidly and are actively invasive, often metastasizing to the lymph nodes. The above-described cancer usually affects Hereford cattle but has been found in Ayrshire, Simmental, Shorthorn, Holstein, and cross-bred animals thereof. Several cattle were successfully treated with a 10–30 Kd peat preparation.

A cow having bovine ocular squamous cell carcinoma was treated by injecting 5 ml of a solution containing 3 mg/ml 10–30 Kd peat preparation into the sarcoma. Ten days later, the tissue firmed up, blood supply increased, and the tumor had shrunk considerably. Three weeks later, there were no visible signs of the tumor remaining.

Another cow was treated using a slightly different treatment regimen. The original lesion measured 5 cm×2½ cm. Initial treatment consisted of debriding the necrotic areas and then suturing four gauze pads over the right eye after injecting 1 ml of a 10–30 Kd peat preparation into the tumor. The gauze was subsequently soaked liberally with the preparation. The soaked gauze was covered, and an eye patch was applied. This treatment procedure was repeated weekly for five weeks. During this time, the size of the tumor was reduced substantially.

A 12-year-old purebred Hereford cow had a squamous cell carcinoma on its upper and lower left eyelids and nictitating membrane. Necrotic tissue was debrided under local anesthesia, a biopsy sample was taken, and 3 ml of the 10–30 Kd peat preparation was injection into the lesion. The examination and treatment were repeated after nine days, and considerable improvement was noted. The treatment was repeated after 49 days. A second growth was found on the right eye, which was also treated. After two months, the cow appeared to be healthy and tumor-free.

Another cow had a squamous cell carcinoma lesion 0.5 $cm^2$ on its corneal limbus. The growth was surgically removed, and then 0.5 ml of 10–30 Kd peat preparation was injected into area. No further treatment was administered until one ear later, when a small plaque was removed.

EXAMPLE 12

Inhibition of Protein Kinase C Activities

PAF was tested for its ability to inhibit PKC by the method of Hannun, et al. (1985) J. Biol, Chem. 260: 10039 and Jeng et al. (1986) Cancer Res. 46: 1966. PAF 10–30K (1 mg/ml) was added to a reaction mixture including 20 mM Tris (pH 7.4), [32P]-ATP, phosphatidylserine, and partially purified protein kinase C (1 mg/ml; approximately $10^{-5}$M) from rat brain. Following a 10-minute incubation, 25 ul aliquots were removed, spotted on phosphocellulose paper, washed three times in cold phosphoric acid, dried, and counted to determine the product formed. The results indicate that PAF 10–30K inhibited 100 percent of PKC activities at the test dose.

EXAMPLE 13

Effects of PAF on Various Protein Kinases

PAF 10–30K was tested for its effects on kinase activities using cyclothymic extracts of EL4 wild-type thymoma cells. Extracts of phorbol ester-treated cells were used for MBP (myelin basic protein kinase) and S6P (Kemptide kinase) assays.

Assays on these kinases were carried out using PAF 10–30K extracts of Bonaparte peat (BPAF 10–30K), which had been lyophilized and reconstituted by suspension in water. The activity is illustrated in Table 1. All three kinases were inhibited at similar concentrations.

TABLE 1

| PAF Concentration | % of Control | | |
|---|---|---|---|
| mg/ml) | PKC | MBP | S6P |
| 0.05 | 70% | | |
| 0.1 | 88 | 70% | 100% |
| 0.5 | 95 | 35 | 75 |
| 1.0 | 40 | 18 | 68 |
| 5.0 | 0 | 0 | 18 |
| 10.0 | 0 | 0 | 0 |

EXAMPLE 14

Effects of PAF on Syntide-2 Kinase Activities

Syntide-2 is a substrate for $Ca^{++}$/calmodulin-dependent protein kinase II and is stimulated by $Ca^{++}$. Like the other kinases mentioned in these examples, it is contained in the cyclothymic extracts prepared from EL4 thymoma cells. Syn-2 kinase activity was markedly stimulated by PAF at low doses in the presence and absence and absence of $Ca^{++}$ (Table 2). This stimulation occurs at doses much lower than the dose influencing the PKC, MBP, and S6P kinases.

TABLE 2

Effects on Syntide-2 K
% of Control Counts/Min of
Syntide-2 Phosphorylation

| PAF Concentration (mg/ml) | Without $Ca^{++}$ | With $Ca^{++}$ |
|---|---|---|
| 0.10 | 370% | 420% |
| 0.25 | 650 | — |
| 0.30 | — | 430 |
| 1.00 | 550 | 200 |

EXAMPLE 15

Effect of Bonaparte and Humic Acid PAF on Kinases

PAF prepared from a humic acid and made to a 1 percent concentration gave a 45.6 percent inhibition of PKC, 95 percent inhibition of MBP, and 62 percent inhibition of S6P kinases. In a similar assay, 0.04 percent solution of PAF prepared from Bonaparte peat of molecular weight above 10,000 daltons gave a 60 percent inhibition of MBP.

EXAMPLE 16

Effect of PAF from Other Peat Sources on Kinases

Table 3 shows the effect of PAF from Alberta, Manitoba, and Bonaparte peats on PKC, S6P, and MBP as shown by phosphokinase phosphorylation. It can be seen that each PAF possessed activity that varied, depending on the peat source.

TABLE 3

| PAF Concentration | [32] Phosphorylation Counts/Min | | |
|---|---|---|---|
| (mg/ml) | PKC | MBP | S6P |
| PAF from Bonaparte Peat | | | |
| 0 | 57,000 | 20,000 | 8,000 |
| $2 \times 10^{-4}$ | 57,000 | 16,000 | 10,000 |
| $2 \times 10^{-3}$ | 75,000 | 6,000 | 18,000 |
| $10 \times 10^{-3}$ | — | — | 25,000 |
| $2 \times 10^{-2}$ | 90,000 | 3,000 | 5,000 |
| PAF from Alberta Peat | | | |
| $2 \times 10^{-4}$ | 35,000 | | 5,000 |
| $10 \times 10^{-4}$ | 55,000 | | 12,000 |
| $2 \times 10^{-3}$ | 48,000 | | 13,000 |
| $10 \times 10^{-3}$ | 45,000 | | 15,000 |
| $2 \times 10^{-2}$ | 15,000 | | 8,000 |
| PAF from Manitoba Peat | | | |
| $2 \times 10^{-4}$ | 40,000 | 15,000 | 11,000 |
| $10 \times 10^{-4}$ | 70,000 | 14,000 | 13,000 |
| $2 \times 10^{-3}$ | 55,000 | 7,500 | 12,000 |
| $10 \times 10^{-3}$ | 25,000 | 5,000 | 13,000 |
| $2 \times 10^{-2}$ | — | — | — |

EXAMPLE 17

Effects of PAF on Calmodulin Kinase II

Using the BPAF 10–30K from Example 2, a 430 percent increase in CaM K-II activity was observed at a BPAF concentration of 0.1 mg/ml.

EXAMPLE 18

Effects of PAF on Red Blood Cell Membrane ATP'ases

ATP'ase assays were carried out by calorimetric determination of the inorganic phosphate, according to the method of Raess and Vincenzi, J. Pharmacological Methods, 1980, 391 and Vincenzi, et al., Hypertension, 1986, 1058. ATP'ase assays were carried out in a total of 0.1 ml in flat-bottom 96 well plates. 400 uL of sample were used. ATP was added to start the reaction, which was carried out for 60 minutes at 37° C. The reaction was terminated by the addition of SDS (0.83 percent), and inorganic phosphate was then determined.

ATP'ases were operationally defined as the Ca pump ATP'ase (measured in basal and calmodulin activated states), the Na/K pump ATP'ase, and the Mg-ATP'ase. Mg-ATP'ase was defined as the activity in the presence of histidine-imidazole buffer (18/18 mM), Na (80 mM), K (15 mM), Mg (3 mM), EGTA (0.1 mM), and ouabain (0.1 mM). Na/K pump ATP'ase activity was defined in the same medium but in the absence of added ouabain. Basal Ca pump activity was defined in the presence of ouabain and with added Ca (0.2 mM added, 0.1 mM in excess of EGTA); calmodulin activated Ca pump ATP'ase activity was defined by the addition of calmodulin (30 nM). The specific activity of the Na/K ATP'ase was 5.8 M/min/mg protein; that of the basal Ca ATP'ase was 10.5 nM/min/mg protein; that of the CaM activated Ca pump ATP'ase was 59.3 nM/min/mg protein; and that of the Mg-ATP'ase was 4.6 nM/min/mg protein.

Table 4 demonstrates the activity of the different PAF molecular weight fractions on calcium—calmodulin—at sodium/potassium—ATP'ases.

TABLE 4

Effects of PAF on Various ATP'ases

| | PAF Concentration | % Stimulation or Inhibition of Indicated ATP'ases | | |
|---|---|---|---|---|
| | mg/ml | $Ca^{++1}$ | $CaM^2$ | $Na^+/$ |
| SE | $7 \times 10^{-2}$ | −34 | −34 | 3 |
| PAF >30K | $4 \times 10^{-2}$ | −51 | −45 | −5 |
| PAF <30K | $30 \times 10^{-2}$ | −63 | −60 | −43 |
| PAF 10–30K | $6 \times 10^{-2}$ | −100 | −100 | −62 |
| PAF >10K | $30 \times 10^{-2}$ | −100 | −100 | −75 |
| PAF <10K | $30 \times 10^{-2}$ | 5 | −12 | −17 |
| PAF 2–10K | $20 \times 10^{-2}$ | 94 | 16 | 17 |
| PAF <2K | $20 \times 10^{-2}$ | 27 | 1 | −24 |
| PAF 0.5–2K | $20 \times 10^{-2}$ | 10 | −5 | 13 |
| PAF <0.5K | $10 \times 10^{-2}$ | 13 | −18 | −27 |

[1]Basal (calmodulin free) Ca pump ATP'ase
[2]Calmodulin-activated Ca pump ATP'ase Table 5 demonstrates the activity of PAF on magnesium ATP'ase.

TABLE 5

Effects of PAF on Mg ATP'ase

| | PAF Concentration mg/ml | % Stimulation or Inhibition (−) of Mg ATP'ase $Mg^{++}$ |
|---|---|---|
| SE | $4 \times 10^{-2}$ | 15 |
| | $1 \times 10^{-2}$ | −48 |
| PAF 10–30K[1] | $30 \times 10^{-1}$ | 30 |
| | $6 \times 10^{-2}$ | 25 |
| PAF < 2K[1] | $20 \times 10^{-2}$ | 50 |
| PAF 0.5–2K[1] | $20 \times 10^{-2}$ | 26 |
| | $0.6 \times 10^{-2}$ | −27 |
| PAF < 0.5K[1] | $10 \times 10^{-2}$ | 27 |

[1]After acid treatment and removal of solids

Table 6 demonstrates the activity of PAFs isolated from different sources of peat and peat-derived materials.

TABLE 6

Effects of PAF from Various Peat and Related Sources on Various ATP'ases

| | PAF Concentration | % Stimulation or Inhibition (−) of Indicated ATP'ases | | | |
|---|---|---|---|---|---|
| | mg/ml | $Ca^{++1}$ | $CaM^2$ | $Mg^{++}$ | $Na^+/K^+$ |
| Bonaparte PAF 10–30K | $6 \times 10^{-2}$ | −100 | −100 | −55 | −62 |
| Alberta PAF 10–30K | $8 \times 10^{-2}$ | −65 | −70 | 57 | −70 |
| Manitoba PAF 10–30K | $8 \times 10^{-2}$ | −100 | −96 | 51 | −77 |
| N. America[3] PAF 10–30K | $16 \times 10^{-2}$ | −71 | −79 | −14 | −22 |
| Leonardite[4] SE | $11 \times 10^{-2}$ | −100 | −100 | −67 | −72 |

TABLE 6-continued

Effects of PAF from Various Peat and Related Sources on Various ATP'ases

| | PAF Concentration | % Stimulation or Inhibition (−) of Indicated ATP'ases | | | |
|---|---|---|---|---|---|
| | mg/ml | $Ca^{++1}$ | $CaM^2$ | $Mg^{++}$ | $Na^+/K^+$ |
| Humic Acids PAF 10–30K | $2 \times 10^{-2}$ | −67 | −84 | −68 | −9 |

[1]Basal (calmodulin free) Ca pump ATP'ase
[2]Calmodulin-activated Ca pump ATP'ase
[3]Extract of reed and sedge peats from North Carolina, New Jersey, Minnesota, and Saskatchewan
[4]A commercial leonardite solution adjusted to pH 7 for testing Addition of the 10–30,000 dalton extracts from Bonaparte, Manitoba, and Alberta peats to the assay mixtures at the conclusion of the incubation had a negligible effect on the results, showing that the compounds do not interfere with the assay. The compounds do not appear to compete for binding of ATP to the kinases.

Table 7 demonstrates the activity of PAF isolated by heat extraction.

TABLE 7

Effects of Heat-Extracted PAF on Various ATP'ases

| | PAF Concentration | % Stimulation or Inhibition (−) of Indicated ATP'ases | | | |
|---|---|---|---|---|---|
| | mg/ml | $^1Ca^{++}$ | $^2CaM$ | $Mg^{++}$ | $Na^+/K^+$ |
| S.B.E. | $3 \times 10^{-2}$ | −73 | −93 | 210 | −83 |
| | $0.3 \times 10^{-2}$ | −90 | −87 | 0 | −50 |
| | $0.93 \times 10^{-2}$ | −87 | −27 | 0 | −67 |

[1]Basal (calmodulin free) Ca pump ATP'ase
[2]Calmodulin-activated Ca pump ATP'ase Table 8 demonstrates the activity of lyophilized PAF.

TABLE 8

Effects of Heat-Extracted PAF on Various ATP'ases

| | PAF Concentration | % Stimulation or Inhibition (−) of Indicated ATP'ases | | | |
|---|---|---|---|---|---|
| | mg/ml | $^1Ca^{++}$ | $^2CaM$ | $M^{++}$ | $Na^+/K^+$ |
| PAF 10–30K | $15 \times 10^{-2}$ | −72 | −84 | 50 | −45 |
| | $6 \times 10^{-2}$ | −48 | −59 | 12 | −25 |
| | $3 \times 10^{-2}$ | −26 | −32 | −6 | −18 |
| PAF 10–30K[3] | $15 \times 10^{-2}$ | −79 | −87 | −61 | −31 |
| | $6 \times 10^{-2}$ | −65 | −70 | −19 | −32 |
| | $3 \times 10^{-2}$ | −29 | −34 | −26 | −1 |

[1]Basal (calmodulin free) Ca pump ATP'ase
[2]Calmodulin-activated Ca pump ATP'ase
[3]Lyophilized and reconstituted in water

EXAMPLE 19

Effect of PAF on Tissue Cell Growth

BPAF 10–30K was tested for its effect on proliferation of nonmalignant neurological andromyelin blastoma cell lines. Concentrations of $2 \times 10^{-4}$ and $2 \times 10^{-6}$ produced, respectively, 371 percent and 142 percent increases in colonies on a plate compared to controls. PAF from Manitoba peat, at the same concentrations, gave 43 percent and 76 percent increases compared to controls.

EXAMPLE 20

Diuretic and Cardiovascular Effects of PAF

Doses of 2, 8, and 10 mg of BPAF 10–30K were administered into the jugular vein of a 125-lb. sheep, and activity was checked every 15 minutes. The urine volume increased from 56 to 140 ml, the systolic blood pressure increased from 93 to 118 mm, the diastolic blood pressure increased from 68 to 83 mm, and the main arterial pressure increased from 79 to 98 mm. The cardiac output increased from about 4.9 liters per minute to about 5.8 liters per minute. Systemic vascular resistance increased from about 1200 to 1657. The increase in cardiac output and systemic vascular resistance indicate that heart rate increased.

EXAMPLE 21

Topical Formulations of Purified Peat Compositions

A. 5 ml of the purified peat composition continuing PAF 10–30K solution of Example 2 was shaken with 5 ml of a commercial skin lotion. A stable fluid emulsion resulted.

B. 6.9 parts lyophilized PAF 10–30K solid is dissolved in 93.1 parts PEGO 3350 base with warming and stirring.

|  | Ingredient | Percent by Weight |
| --- | --- | --- |
| Phase A: | Mineral oil | 4.0–7.0 |
|  | Stearic acid | 1.0–4.0 |
|  | Isopropyl palmatate | 0.5–1.0 |
|  | Stearyl alcohol | 0.5–1.0 |
|  | Cetyl alcohol | 1.5–2.5 |
|  | Sorbitan stearate | 0.5–2.5 |
|  | Polysorbate 60 | 0.5–1.0 |
|  | Synthetic beeswax | 0.5–2.0 |
|  | Preservative | 0.1–0.3 |
| Phase B: | Water | 83.3–37.4 |
|  | Triethanolamine | 0.3–1.0 |
|  | Glycerine | 2.0–5.0 |
|  | Preservative | 0.1–0.3 |
| Phase C: | Compound | 0.1–10.0 |
|  | Triethanolamine | 0.2–10.0 |
|  | Water | 5.0–15.0 |

Phase A ingredients are heated to 75° C. and mixed well. This first mixture is maintained at 75° C. with continuous agitation. The Phase B ingredients are mixed and stirred for 15 minutes at 70° C. This second mixture is maintained at 50° C. with stirring. Phase A and Phase B are combined and stirred for 15 minutes at 70° C. The mixture is then maintained at 50° C. with stirring. Phase C is made by mixing compound and triethanolamine.

The examples presented above are to be considered in all respects as illustrative and not restrictive. The scope of the invention is indicated by the appended claims only, and all modifications that come within the meaning and equivalency of the claims therefore are intended to be embraced therein.

What is claimed is:

1. A pharmaceutically acceptable composition comprising an aqueous, organic, or water-miscible organic extract of Hypnum peat, wherein the extract includes peat materials essentially consisting of components each having a molecular weight of less than 30,000 Daltons, and wherein at least one of the components is a therapeutically effective component having therapeutic activity against pruritis, inflammation, psoriasis, eczema, rheumatoid arthritis, shingles, athlete's foot, acne, or conjunctivitis.

2. A composition according to claim 1, wherein the extract is an alkaline extract of peat.

3. A composition according to claim 1, wherein the extract is an extract of Bonaparte peat.

4. A composition of claim 1, wherein the therapeutically effective component is derived from peat materials eluted in a fraction of a fractional separation of the extract, wherein the fraction contains gypsum, syngenite, or aphthitalite.

5. A composition according to claim 1, further comprising a carrier or diluent.

6. A composition of claim 1, wherein the therapeutically effective component is derived from a peat fraction having peat materials essentially consisting of components each having a molecular weight of greater than about 10,000 Daltons.

7. A composition of claim 1, wherein the therapeutically effective component is derived from a peat fraction having peat materials essentially consisting of components each having a molecular weight of less than about 10,000 Daltons.

8. A composition of claim 1, wherein the therapeutically effective component is derived from a peat fraction having peat materials essentially consisting of components each having a molecular weight of between about 500 and 2,000 Daltons.

9. A composition of claim 1, wherein the therapeutically effective component is derived from a peat fraction having peat materials essentially consisting of components each having a molecular weight of less than about 500 Daltons.

10. A method for the treatment of skin diseases by administration of a pharmaceutically acceptable composition according to claim 4, comprising the topical administration of a therapeutically effective amount of the peat fraction in conjunction with a pharmaceutically acceptable carrier.

11. A cosmetic preparation, comprising a dermatalogically acceptable composition, comprising:

an elutant fraction of an aqueous, organic, or water-miscible organic extract of Hypnum peat, wherein the extract includes peat materials essentially consisting of components each having a molecular weight of less than 30,000 Daltons and the elutant fraction includes gypsum, syngenite, or aphthitalite.

12. A composition according to claim 5, wherein the carrier or diluent comprises glycerol.

13. A composition according to claim 5, wherein the carrier or diluent comprises a topical cream.

14. A composition according to claim 5 wherein the extract comprises a complex of a calcium-containing component, a potassium-containing component, and a sulfate-containing component, the calcium-containing component and the sulfate-containing component being bound to one another covalently or non-covalently in the carrier or diluent.

15. A composition according to claim 14, comprising a complex of a calcium-containing component and potassium sulfate.

16. A composition according to claim 15, wherein the calcium-containing component is calcium sulfate.

17. A composition according to claim 16, wherein the complex of calcium sulfate and potassium sulfate is syngenite.

18. A composition according to claim 1, comprising a complex of potassium-sodium-sulfate.

19. A composition according to claim 18, wherein the complex of potassium-sodium-sulfate is aphthitalite ($K_3Na(SO_4)_2$).

20. A composition according to claim 1, wherein at least one of the components is a therapeutically effective component having therapeutic activity against rheumatoid arthritis.

21. A preparation according to claim 11, wherein at least one of the components is a therapeutically effective component having therapeutic activity against rheumatoid arthritis.

22. A composition according to claim 1, wherein at least one of the components is a therapeutically effective component having therapeutic activity against inflammation.

23. A preparation according to claim 11, wherein at least one of the components is a therapeutically effective component having therapeutic activity against inflammation.

24. A composition according to claim 1, wherein at least one of the components is a therapeutically effective component having therapeutic activity against conjunctivitis.

25. A preparation according to claim 11, wherein at least one of the components is a therapeutically effective component having therapeutic activity against conjunctivitis.

26. A composition according to claim 4, wherein the fraction of the extract has therapeutic activity against pruritis, inflammation, psoriasis, eczema, rheumatoid arthritis, shingles, athlete's foot, acne, or conjunctivitis.

* * * * *